US011111537B2

(12) United States Patent
Kassis

(10) Patent No.: US 11,111,537 B2
(45) Date of Patent: *Sep. 7, 2021

(54) METHODS OF DETECTING AUTOIMMUNE OR IMMUNE-RELATED DISEASES OR CONDITIONS

(71) Applicant: President and Fellows of Harvard College, Cambridge, MA (US)

(72) Inventor: Amin I. Kassis, Chestnut Hill, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/014,476

(22) Filed: Feb. 3, 2016

(65) Prior Publication Data

US 2016/0153984 A1 Jun. 2, 2016

Related U.S. Application Data

(63) Continuation of application No. 13/811,695, filed as application No. PCT/US2011/044973 on Jul. 22, 2011, now abandoned.

(60) Provisional application No. 61/367,018, filed on Jul. 23, 2010.

(51) Int. Cl.
| | |
|---|---|
| *C12Q 1/6883* | (2018.01) |
| *G01N 33/564* | (2006.01) |
| *C12Q 1/02* | (2006.01) |

(52) U.S. Cl.
CPC ............ *C12Q 1/6883* (2013.01); *C12Q 1/02* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01); *C12Q 2600/16* (2013.01); *C12Q 2600/178* (2013.01); *G01N 33/564* (2013.01); *G01N 2500/10* (2013.01); *G01N 2800/24* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,814,434 | A | 3/1989 | Goldfarb |
| 4,843,155 | A | 6/1989 | Chomczynski |
| 4,868,103 | A | 9/1989 | Stavrianopoulos et al. |
| 5,043,267 | A | 8/1991 | Richards |
| 5,077,216 | A | 12/1991 | Morganelli et al. |
| 5,459,039 | A | 10/1995 | Modrich et al. |
| 5,498,531 | A | 3/1996 | Jarrell |
| 5,514,598 | A | 5/1996 | Doody |
| 5,594,637 | A | 1/1997 | Eisenberg et al. |
| 5,631,169 | A | 5/1997 | Lakowicz et al. |
| 5,854,033 | A | 12/1998 | Lizardi |
| 6,117,985 | A | 9/2000 | Thomas et al. |
| 6,172,198 | B1 | 1/2001 | Sinosich |
| 6,258,540 | B1 | 7/2001 | Lo et al. |
| 6,631,330 | B1 | 10/2003 | Poynard |
| 6,660,477 | B2 | 12/2003 | Kluwe |
| 6,664,056 | B2 | 12/2003 | Lo et al. |
| 6,867,236 | B1 | 3/2005 | Breitner et al. |
| 6,986,995 | B2 | 1/2006 | Rose et al. |
| 7,009,038 | B2 | 3/2006 | Depre et al. |
| 7,157,235 | B2 | 1/2007 | Breit et al. |
| 7,235,359 | B2 | 6/2007 | Lo et al. |
| 7,294,465 | B2 | 11/2007 | Somlo et al. |
| 7,432,107 | B2 | 10/2008 | Spanuth |
| 7,445,886 | B2 | 11/2008 | Giroir et al. |
| 7,459,280 | B2 | 12/2008 | Wang et al. |
| 7,488,584 | B2 | 2/2009 | Wang et al. |
| 7,604,948 | B2 | 10/2009 | Amaral et al. |
| 7,645,576 | B2 | 1/2010 | Lo et al. |
| 7,651,838 | B2 | 1/2010 | Paterlini-Brechot |
| 7,655,399 | B2 | 2/2010 | Cantor et al. |
| 7,662,578 | B2 | 2/2010 | Devarajan |
| 7,670,764 | B2 | 3/2010 | Oh et al. |
| 7,670,769 | B2 | 3/2010 | Lee |
| 7,723,117 | B2 | 5/2010 | Delacourte et al. |

(Continued)

FOREIGN PATENT DOCUMENTS

| | | |
|---|---|---|
| CN | 1668922 A | 9/2005 |
| EP | 2161577 A1 | 3/2010 |

(Continued)

OTHER PUBLICATIONS

Simpson et al. "Proteomic profiling of exosomes: Current perspectives", Proteomics 2008, 8, 4093-4099.
Lu et al. "MicroRNA expression profiles classify human cancers", Nature vol. 435, Jun. 9, 2005. 834-838. DOI: 10.1038/nature03702.
Office Action issued in corresponding Korean Application No. 10-2010-7018216, dated Mar. 7, 2016.
Hoshikawa et al.; Hypoxia induces different genes in the lungs of rats compared with mice; Physical Genomics 2003 vol. 12 pp. 209-219.
Huber, W., et al., Variance Stabilization Applied to Microarray Data Calibration and to the Quantification of Differential Expression, Bioinforrnatics, vol. 18, Suppl. 1, 2002 S96-S104.
International Search Report and Written Opinion relating to corresponding PCT/US20 11/044973, dated Mar. 13, 2012.

(Continued)

*Primary Examiner* — Carla J Myers
(74) *Attorney, Agent, or Firm* — Nixon Peabody LLP; David S. Resnick; Nicole D. Kling

(57) ABSTRACT

This invention provides methods of using phagocytic cells alone or in combination with non-phagocytic cells in the diagnosis, prognosis, or monitoring of autoimmune or immune-related diseases or conditions. The invention also provides methods of using phagocytic cells alone or in combination with non-phagocytic cells to identify markers of autoimmune or immune-related diseases or conditions.

5 Claims, 14 Drawing Sheets

(56) References Cited

U.S. PATENT DOCUMENTS

| | | |
|---|---|---|
| 2001/0036631 A1* | 11/2001 | McGrath .............. C12Q 1/6883 |
| | | 435/6.14 |
| 2001/0051341 A1 | 12/2001 | Lo et al. |
| 2001/0051344 A1 | 12/2001 | Shalon et al. |
| 2002/0045176 A1 | 4/2002 | Lo et al. |
| 2002/0119118 A1 | 8/2002 | Fong et al. |
| 2002/0192642 A1 | 12/2002 | Lo et al. |
| 2003/0064380 A1 | 4/2003 | Rao et al. |
| 2004/0009518 A1 | 1/2004 | Lo et al. |
| 2004/0038201 A1 | 2/2004 | Nau et al. |
| 2004/0086864 A1 | 5/2004 | Lo et al. |
| 2004/0137452 A1 | 7/2004 | Levett et al. |
| 2004/0203037 A1 | 10/2004 | Lo et al. |
| 2004/0265932 A1 | 12/2004 | Henslee et al. |
| 2005/0130245 A1 | 6/2005 | Houle et al. |
| 2005/0148023 A1 | 7/2005 | Thadhani et al. |
| 2005/0164233 A1 | 7/2005 | Byrne et al. |
| 2005/0164241 A1 | 7/2005 | Hahn et al. |
| 2005/0181386 A1 | 8/2005 | Diamond et al. |
| 2005/0266432 A1 | 12/2005 | Oliphant et al. |
| 2005/0282185 A1 | 12/2005 | Lo et al. |
| 2006/0019278 A1 | 1/2006 | Lo et al. |
| 2006/0051873 A1 | 3/2006 | FitzGerald |
| 2006/0088836 A1 | 4/2006 | Wohlgemuth et al. |
| 2006/0094067 A1 | 5/2006 | Herwig |
| 2006/0115832 A1 | 6/2006 | Hoon |
| 2006/0115854 A1 | 6/2006 | Goldknopf et al. |
| 2006/0115855 A1 | 6/2006 | Goldknopf et al. |
| 2006/0166283 A1 | 7/2006 | Delacourte et al. |
| 2006/0172429 A1 | 8/2006 | Nilsson et al. |
| 2006/0210562 A1 | 9/2006 | Zaghouani et al. |
| 2006/0234301 A1 | 10/2006 | Dotan et al. |
| 2006/0252068 A1 | 11/2006 | Lo et al. |
| 2006/0252071 A1 | 11/2006 | Lo et al. |
| 2006/0257901 A1 | 11/2006 | Karumanchi |
| 2006/0259990 A1 | 11/2006 | Von Der Kammer et al. |
| 2006/0259991 A1 | 11/2006 | Von Der Kammer et al. |
| 2007/0015172 A1 | 1/2007 | Zhang et al. |
| 2007/0037179 A1 | 2/2007 | Liboni et al. |
| 2007/0099209 A1 | 5/2007 | Clarke et al. |
| 2007/0134689 A1 | 6/2007 | Chow |
| 2007/0141625 A1 | 6/2007 | Santos et al. |
| 2007/0148661 A1 | 6/2007 | Vance et al. |
| 2007/0162983 A1 | 7/2007 | Hesterkamp et al. |
| 2007/0207466 A1 | 9/2007 | Cantor et al. |
| 2007/0218469 A1 | 9/2007 | Navon |
| 2007/0218519 A1 | 9/2007 | Urdea et al. |
| 2007/0224638 A1 | 9/2007 | Melanitou-McClymont |
| 2007/0264197 A1 | 11/2007 | Lamping et al. |
| 2007/0275402 A1 | 11/2007 | Lo et al. |
| 2008/0026378 A1 | 1/2008 | Bottazzo et al. |
| 2008/0026405 A1 | 1/2008 | Lovell et al. |
| 2008/0038730 A1 | 2/2008 | Von der Kammer et al. |
| 2008/0039402 A1 | 2/2008 | Mossalayi et al. |
| 2008/0051334 A1 | 2/2008 | Pohlner et al. |
| 2008/0057590 A1 | 3/2008 | Urdea et al. |
| 2008/0108509 A1 | 5/2008 | Haupl et al. |
| 2008/0152589 A1 | 6/2008 | Schofield et al. |
| 2008/0153090 A1 | 6/2008 | Lo et al. |
| 2008/0220013 A1 | 9/2008 | Hochstrasser et al. |
| 2008/0227709 A1 | 9/2008 | Pascual et al. |
| 2008/0261226 A1 | 10/2008 | Wang et al. |
| 2008/0269103 A1 | 10/2008 | Von Der Kammer et al. |
| 2008/0274118 A1 | 11/2008 | Aukerman et al. |
| 2008/0286263 A1 | 11/2008 | Leeds et al. |
| 2009/0023166 A1 | 1/2009 | Jeannin et al. |
| 2009/0041862 A1 | 2/2009 | Schofield et al. |
| 2009/0054321 A1 | 2/2009 | O'Neill et al. |
| 2009/0061425 A1 | 3/2009 | Lo et al. |
| 2009/0104605 A1 | 4/2009 | Siuzdak et al. |
| 2009/0110667 A1 | 4/2009 | Mozaffarian et al. |
| 2009/0130683 A1 | 5/2009 | Gaffney et al. |
| 2009/0155230 A1 | 6/2009 | Salonen et al. |
| 2009/0155776 A1 | 6/2009 | Lo et al. |
| 2009/0162842 A1 | 6/2009 | Lo et al. |
| 2009/0170102 A1 | 7/2009 | Lo et al. |
| 2009/0176217 A1 | 7/2009 | Sella-Tavor et al. |
| 2009/0196927 A1 | 8/2009 | Panitch et al. |
| 2009/0202469 A1 | 8/2009 | Maruyama et al. |
| 2009/0239241 A1 | 9/2009 | Ray et al. |
| 2009/0239242 A1 | 9/2009 | Kilty et al. |
| 2009/0258025 A1 | 10/2009 | Godowski et al. |
| 2009/0263474 A1 | 10/2009 | Banchereau et al. |
| 2009/0263796 A1 | 10/2009 | Wohlgemuth et al. |
| 2009/0274709 A1 | 11/2009 | Xu et al. |
| 2009/0275046 A1 | 11/2009 | Goldknopf et al. |
| 2009/0305265 A1 | 12/2009 | Snider et al. |
| 2009/0317797 A1 | 12/2009 | Paterlini et al. |
| 2009/0318354 A1 | 12/2009 | Cahill et al. |
| 2009/0318392 A1 | 12/2009 | Oresic et al. |
| 2009/0324611 A1 | 12/2009 | Eriksson |
| 2010/0009352 A1 | 1/2010 | Gough et al. |
| 2010/0009356 A1 | 1/2010 | Snider et al. |
| 2010/0021929 A1 | 1/2010 | Pow |
| 2010/0028356 A1 | 2/2010 | Schofield et al. |
| 2010/0055722 A1 | 3/2010 | Nayak et al. |
| 2010/0056523 A1 | 3/2010 | Heerding et al. |
| 2010/0062463 A1 | 3/2010 | Bergmann et al. |
| 2010/0068705 A1 | 3/2010 | Helgadottir et al. |
| 2010/0068711 A1 | 3/2010 | Umansky et al. |
| 2010/0075891 A1 | 3/2010 | Ayalon-Soffer et al. |
| 2010/0081142 A1 | 4/2010 | Chen et al. |
| 2010/0092983 A1 | 4/2010 | Liew |
| 2010/0098705 A1 | 4/2010 | Eugen-Olsen et al. |
| 2010/0104579 A1 | 4/2010 | Hubner et al. |
| 2010/0105086 A1 | 4/2010 | Landolfo et al. |
| 2010/0105623 A1 | 4/2010 | Weinberger et al. |
| 2010/0112587 A1 | 5/2010 | Hare et al. |
| 2010/0120041 A1 | 5/2010 | Quaggin |
| 2010/0120050 A1 | 5/2010 | Gadkar et al. |
| 2010/0120056 A1 | 5/2010 | Bar-Or et al. |
| 2010/0120076 A1 | 5/2010 | Braun et al. |
| 2010/0120629 A1 | 5/2010 | Ellis et al. |
| 2010/0124746 A1 | 5/2010 | Liew |
| 2010/0124756 A1 | 5/2010 | Ray et al. |
| 2010/0131286 A1 | 5/2010 | Houlgatte et al. |
| 2010/0137263 A1 | 6/2010 | Smith |
| 2010/0137393 A1 | 6/2010 | Bottazzo et al. |
| 2010/0143951 A1 | 6/2010 | Kronenberg et al. |
| 2010/0159486 A1 | 6/2010 | Liotta et al. |
| 2010/0167320 A1 | 7/2010 | Beemink et al. |
| 2010/0167937 A1 | 7/2010 | Goldknopf et al. |
| 2010/0169988 A1 | 7/2010 | Kohli et al. |
| 2010/0184031 A1 | 7/2010 | Raes et al. |
| 2011/0033839 A1 | 2/2011 | Kassis |
| 2011/0251097 A1 | 10/2011 | Song et al. |
| 2012/0021404 A1 | 1/2012 | Melkonyan et al. |
| 2012/0040846 A1 | 2/2012 | Kassis |
| 2012/0053073 A1 | 3/2012 | Kassis |
| 2018/0258488 A1 | 9/2018 | Kassis |

FOREIGN PATENT DOCUMENTS

| | | |
|---|---|---|
| JP | H11118792 A | 4/1999 |
| JP | H11295304 A | 10/1999 |
| JP | 2005-531785 A | 10/2005 |
| JP | 2007211020 A | 8/2007 |
| KR | 20100044307 A | 4/2010 |
| WO | 1994/016101 A2 | 7/1994 |
| WO | 0114881 A1 | 3/2001 |
| WO | 2002/028999 A2 | 4/2002 |
| WO | 2002/070748 A2 | 9/2002 |
| WO | 02068685 A2 | 9/2002 |
| WO | 03019193 A1 | 3/2003 |
| WO | 2004/024098 A2 | 3/2004 |
| WO | 2004/040016 A2 | 5/2004 |
| WO | 2004/050704 A1 | 6/2004 |
| WO | 2004/071269 A2 | 8/2004 |
| WO | 2004/076639 A2 | 9/2004 |
| WO | 2004/079012 A1 | 9/2004 |
| WO | 2005/007836 A1 | 1/2005 |
| WO | 2005/012907 A1 | 2/2005 |
| WO | 2005017192 A2 | 2/2005 |
| WO | 2005/020784 A2 | 3/2005 |

(56) References Cited

FOREIGN PATENT DOCUMENTS

| | | |
|---|---|---|
| WO | 2005/033341 A2 | 4/2005 |
| WO | 2005/052592 A2 | 6/2005 |
| WO | 2005/095644 A2 | 10/2005 |
| WO | 2005/103712 A2 | 11/2005 |
| WO | 2005/111626 A2 | 11/2005 |
| WO | 2005/114222 A1 | 12/2005 |
| WO | 2006/020269 A2 | 2/2006 |
| WO | 2006/020899 A2 | 2/2006 |
| WO | 2006/026020 A2 | 3/2006 |
| WO | 2006/048778 A1 | 5/2006 |
| WO | 2006/050475 A2 | 5/2006 |
| WO | 2006/061609 A2 | 6/2006 |
| WO | 2006/073941 A2 | 7/2006 |
| WO | 2006/105907 A1 | 10/2006 |
| WO | 2006/114661 A1 | 11/2006 |
| WO | 2006/125117 A2 | 11/2006 |
| WO | 2006/133423 A1 | 12/2006 |
| WO | 2006/134390 A2 | 12/2006 |
| WO | 2007/047907 A2 | 4/2007 |
| WO | 2007/082733 A1 | 7/2007 |
| WO | 2007076411 A1 | 7/2007 |
| WO | 2007/098585 A1 | 9/2007 |
| WO | 2007/112999 A2 | 10/2007 |
| WO | 2007/119179 A2 | 10/2007 |
| WO | 2007/131345 A1 | 11/2007 |
| WO | 2008/003826 A1 | 1/2008 |
| WO | 2008/010660 A1 | 1/2008 |
| WO | 2008/014314 A2 | 1/2008 |
| WO | 2008/014516 A2 | 1/2008 |
| WO | 2008/028257 A1 | 3/2008 |
| WO | 2008/042012 A1 | 4/2008 |
| WO | 2008/043725 A1 | 4/2008 |
| WO | 2008/043782 A2 | 4/2008 |
| WO | 2008/046509 A1 | 4/2008 |
| WO | 2008/046510 A1 | 4/2008 |
| WO | 2008/046511 A1 | 4/2008 |
| WO | 2008/046512 A1 | 4/2008 |
| WO | 2008/063369 A2 | 5/2008 |
| WO | 2008/064336 A2 | 5/2008 |
| WO | 2008/082519 A2 | 7/2008 |
| WO | 2008/084331 A2 | 7/2008 |
| WO | 2008/085035 A1 | 7/2008 |
| WO | 2008/089936 A1 | 7/2008 |
| WO | 2008/095261 A1 | 8/2008 |
| WO | 2008/100596 A2 | 8/2008 |
| WO | 2008/120684 A1 | 10/2008 |
| WO | 2008/125651 A2 | 10/2008 |
| WO | 2008/127317 A2 | 10/2008 |
| WO | 2008/129296 A2 | 10/2008 |
| WO | 2008/132464 A2 | 11/2008 |
| WO | 2008/137835 A2 | 11/2008 |
| WO | 2008/147938 A2 | 12/2008 |
| WO | 2008/154238 A1 | 12/2008 |
| WO | 2008/156867 A1 | 12/2008 |
| WO | 2009/000520 A1 | 12/2008 |
| WO | 2009/001392 A1 | 12/2008 |
| WO | 2009/003142 A1 | 12/2008 |
| WO | 2009/014639 A2 | 1/2009 |
| WO | 2009/017444 A2 | 2/2009 |
| WO | 2009/032722 A1 | 3/2009 |
| WO | 2009/034470 A2 | 3/2009 |
| WO | 2009/043848 A2 | 4/2009 |
| WO | 2009/050444 A1 | 4/2009 |
| WO | 2009/053523 A1 | 4/2009 |
| WO | 2009/053537 A1 | 4/2009 |
| WO | 2009/055487 A1 | 4/2009 |
| WO | 2009/058168 A1 | 5/2009 |
| WO | 2009/059259 A2 | 5/2009 |
| WO | 2009/060035 A1 | 5/2009 |
| WO | 2009/068591 A2 | 6/2009 |
| WO | 2009/074331 A2 | 6/2009 |
| WO | 2009/075566 A1 | 6/2009 |
| WO | 2009/075579 A1 | 6/2009 |
| WO | 2009/080780 A1 | 7/2009 |
| WO | 2009/083950 A2 | 7/2009 |
| WO | 2009/092068 A1 | 7/2009 |
| WO | 2009/092382 A1 | 7/2009 |
| WO | 2009/097450 A1 | 8/2009 |
| WO | 2009/100131 A2 | 8/2009 |
| WO | 2009/100342 A2 | 8/2009 |
| WO | 2009/121152 A2 | 10/2009 |
| WO | 2009/121951 A1 | 10/2009 |
| WO | 2009/122387 A1 | 10/2009 |
| WO | 2009/127644 A1 | 10/2009 |
| WO | 2010/005750 A2 | 1/2010 |
| WO | 2010/011506 A2 | 1/2010 |
| WO | 2010/012306 A1 | 2/2010 |
| WO | 2010/018185 A1 | 2/2010 |
| WO | 2010/019553 A2 | 2/2010 |
| WO | 2010/022210 A2 | 2/2010 |
| WO | 2010/024776 A1 | 3/2010 |
| WO | 2010/025434 A1 | 3/2010 |
| WO | 2010/039714 A1 | 4/2010 |
| WO | 2010/041046 A2 | 4/2010 |
| WO | 2010/046137 A1 | 4/2010 |
| WO | 2010/046503 A2 | 4/2010 |
| WO | 2010/047448 A1 | 4/2010 |
| WO | 2010/048346 A1 | 4/2010 |
| WO | 2010/048347 A2 | 4/2010 |
| WO | 2010/048497 A1 | 4/2010 |
| WO | 2010/053587 A2 | 5/2010 |
| WO | 2010/054167 A2 | 5/2010 |
| WO | 2010/054389 A1 | 5/2010 |
| WO | 2010/059242 A2 | 5/2010 |
| WO | 2010/059996 A1 | 5/2010 |
| WO | 2010/061283 A2 | 6/2010 |
| WO | 2010/063009 A1 | 6/2010 |
| WO | 2010/066000 A1 | 6/2010 |
| WO | 2010/068686 A2 | 6/2010 |
| WO | 2012/012693 A2 | 1/2012 |
| WO | 2012/012694 A2 | 1/2012 |
| WO | 2012/012704 A2 | 1/2012 |
| WO | 2012/012709 A2 | 1/2012 |
| WO | 2012/012714 A2 | 1/2012 |
| WO | 2012/012717 A1 | 1/2012 |
| WO | 2012012725 A2 | 1/2012 |
| WO | 2012/115885 A1 | 8/2012 |

OTHER PUBLICATIONS

International Search Report and Written Opinion relating to corresponding PCT/US2009/031395, dated Mar. 30, 2009.
International Search Report and Written Opinion relating to corresponding PCT/US2011/044969, dated Mar. 23, 2012.
International Search Report and Written Opinion relating to corresponding PCT/US2011/044991, dated Mar. 16, 2012.
International Search Report and Written Opinion relating to corresponding PCT/US2011/044996, dated Mar. 14, 2012.
International Search Report and Written Opinion relating to corresponding PCT/US2011/0450002, dated Mar. 15, 2012.
International Search Report and Written Opinion relating to corresponding PCT/US2011/045009, dated Dec. 14, 2011.
International Search Report and Written Opinion relating to corresponding PCT/US2011/045018, dated Mar. 6, 2012.
Kassis, A., et al., "Antibody-Dependant Signal Amplification in Tumor Xenografts after Pretreatment with Biotinylated Monoclonal Antibody and Avidin or Streptavidin," J. Nucl. Med. 1996, 37:343-352.
Kravtsov, A., et al., "Flow Cytofluorometric Assay of Human Whole Blood Leukocyte DNA Degradation in Response to Yersinia Pestis and *Staphylococcus aureus*." Abstract.
Lau, Sean K. et al. A Specific Marker of Macrophages in Paraffin-Embedded Tissue Samples. Am J Clin Pathol 2004; 122:794-801.
Lee, Jae K., "Analysis Issues for Gene Expression Array Data," Clinical Chemistry, 47:8, 1350-1352 (2001).
Lin, M., et al., "Decreased Expression of Cellular Prostatic Acid Phosphatase Increases Tumorigenicity of Human Prostate Cancer Cells," The Journal of Urology, vol. 166, 1943-1950, Nov. 2001.
Linehan et al.; The Genetics Basis of Cancer of the Kidney; The Jouranl of Urology vol. 170 2163-2172 Dec. 2003.

(56) References Cited

OTHER PUBLICATIONS

Liotta, L., et al., "Cancer's Deadly Signature," Nature Genetics, vol. 33, Jan. 2003.
Liu et al.; Comparison of differentially expressed genes in T lymphocytes between human autoimmune disease and murine models of autoimmune disease; Clinical Immunology. 2004. 112: 225-230.
Liu, Edison T., "Mechanism-Derived Gene Expression Signatures and Predictive Biomarkers in Clinical Oncology," PNAS, Mar. 8, 2005, vol. 102, No. 10, 3531-3532.
Lobenhofer, E., et al., "Progress in the Application of DNA Microarrays," Environmental Health Perspectives, vol. 109, No. 9, Sep. 2001.
Loring et al.; A Gene Expression Profile of Alzheimer's Disease; (DNA and Cell Biology vol. 20 No. 11 pp. 683-695 2001).
McLaren, et al., "Antigen-Specific Gene Expression Profiles of Peripheral Blood Mononuclear Cells Do Not Reflect Those off-Lymphocyte Subsets," Clinical and Diagnostic Laboratory Immunology, Sep. 2004, vol. 11, No. 5, 377-982.
McLerran, D., et al., "Analytical Validation of Serum Proteomic Profiling for Diagnosis of Prostate Cancer: Sources of Sample Bias," Clinical Chemistry, 54:1, 44-52, 2008.
Michiels, et al., "Prediction of Cancer Outcome With Microarrays: A Multiple Random Validation Strategy," Lancet, 2005, 365: 488-492.
Nanni et al.; Differential gene expression profiling in genetic and multifactorial cardiovascular diseases; Journal of Molecular and Cellular Cardiology. 2006. 41 (6): 934-948.
NCBI Bookshelf, Chapter 2, "Chromosomes in Cells," 1999.
Office Action issued for con-esponding AU Patent Application No. 2009205956, dated Sep. 13, 2013.
Office Action issued for corresponding Canadian Patent Application No. 2,712, 303, dated Mar. 19, 2013.
Office Action issued for corresponding Chinese Patent Application No. 200980109695.4, dated Mar. 5, 2013.
Office Action issued for corresponding JP Patent Application No. 2010-543301, dated Aug. 13, 2013.
Office Action issued for corresponding New Zealand Patent Application No. 602007 dated Aug. 24, 2012.
Office Action issued for corresponding U.S. Appl. No. 13/188,683, dated Apr. 23, 2013.
Office Action issued for corresponding U.S. Appl. No. 13/188,683, dated Feb. 21, 2014.
Office Action issued for corresponding U.S. Appl. No. 13/188,964 dated Aug. 14, 2012.
Office Action issued for corresponding U.S. Appl. No. 13/188,964, dated Jun. 4, 2011.
Office Action issued for corresponding U.S. Appl. No. 13/349,670, dated Jun. 7, 2011.
Office Action issued in corresponding Chinese Application No. 200980109695.4 dated Jan. 16, 2014.
Office Action issued in corresponding Chinese Application No. 200980109695.4 dated Sep. 29, 2014.
Office Action issued in corresponding Chinese Application No. 201180046173.1 dated Jan. 28, 2014.
Office Action issued in corresponding Chinese Application No. 201180046173.1, dated Jan. 18, 2016.
Office Action issued in corresponding Chinese Application No. 201180046174.6 dated Feb. 8, 2014.
Office Action issued in corresponding Chinese Patent Application No. 2011800461731, dated Dec. 23, 2014.
Office Action issued in corresponding Eurasian Application No. 201390149, dated Feb. 12, 2015.
Office Action issued in corresponding Eurasian Application No. 201390150, dated Mar. 17, 2015.
Office Action issued in corresponding European Application No. 09703015.9 dated Apr. 22, 2014.
Office Action issued in corresponding European Application No. 09703015.9, dated Jul. 6, 2015.
Office Action issued in corresponding European Application No. 11810446.2 dated Jul. 17, 2014.
Office Action issued in corresponding European Application No. 11810447.0, dated Jan. 21, 2016.
Office Action issued in corresponding European Application No. 11810461.1, dated Dec. 15, 2015.
Office Action issued in corresponding European Application No. 11810457.9, dated Feb. 12, 2015.
Allen, Lee-Ann H.,"Modulating Phagocyte Activation: The Pros and Cons of Helicobacter pylori Virulence Factors," Journal of Experimental Medicine, May 1, 2000, pp. 1451-1454, vol. 191, No. 9, The Rockefeller University Press.
Archacki et al.; Expression profiling of cardiovascular disease; Human Genomics. 1 (5): 355-370.
Avagyan, et al., "Immune Blood Biomarkers of Alzheimer Disease Patients," Journal of Neuroimmunology, 210 (2009) 67-72.
Baker, Stuart G., "The Central Role of Receiver Operating Characteristic (ROC) Curves in Evaluating Tests for the Early Detection of Cancer," Journal of the National Cancer Institute, vol. 95, No. 7, Apr. 2, 2003.
Balagurumoorthy et al., Genome-subtractive cancer-specific blood assay. Cancer Research. AACR Annual Meeting. Apr. 18-22, 2009. Abstract #2562.
Bergsmedh, A., et al. 2006 Molecular Cancer Research 4: 187-195.
Bidwell, Bradley N. et al. Silencing of Irf7 pathways in breast cancer cells promotes bone metastasis through immune escape. Nature Medicine. col. 18, No. 8. Aug. 2012.
Biswas, Subhra K. et al. A distinct and unique transcriptional program expressed by tumor-associated macrophages (defective NF- KB and enhanced IRF-3/STAT1 activation). Blood. Mar. 1, 2006. vol. 101. No. 5.
Bitterman, et al., "Alveolar Macrophage Replication. One Mechanism for the Expansion of the Mononuclear Phagocyte Population in the Chronically Inflamed Lung," The Journal of Clinical Investigations, Inc., vol. 74, Aug. 1984, 460-469.
Caruso, R. A., et al.,2012 Exp Oncol 34: 306-311.
Chakraborty, A., et al., "A Spontaneous Murine Melanoma Lung Metastasis Comprised of Host X Tumor Hybrids," Cancer Research, 60, 2512-2519, May 1, 2000.
Cheung, M., et al., "Prenatal Diagnosis of Sickle Cell Anemia and Thalassaemia by Analysis of Fetal Cells in Maternal Blood," Nature Genetics, vol. 14, Nov. 1996.
Colcher, D., et al., "A Spectrum of Monoclonal Antibodies Reactive with Human Mammary Tumor Cells," Proc. Natl. Acad. Sci. USA, vol. 78, No. 5, pp. 3199-3203, May 1981.
Colcher, D., et al., "Prolonged Binding of a Radiolabeled Monoclonal Antibody (B72.3) Used for the in Situ Radioimmunodetection of Human Colon Carcinoma Xenografts," Cancer Research, 44, 5744-5751, Dec. 1984.
Coleman, R.; Of mouse and man—what is the value of the mouse in predicting gene expression in humans?; Drug Discovery Today. 2003. 8: 233-235.
Denmeade, S., et al., "Concentration of Enzymatically Active Prostate-Specific Antigen (PSA) in the Extracellular Fluid of Primary Human Prostate Cancers and Human Prostate Cancer Xenograft Models," The Prostate 48:1-6, 2001.
Du et al., Genomic profiles for human peripheral blood T cells, B cells, natural killer cells, monocytes, and polymorponuclear cells: Comparisons to ischemic stroke, migrane, and Tourette syndrome, Genomics. 2006. 87: 693-703.
Ehnfors, J., et al., 2009 Cell Death and Differentiation 16: 749-757.
Engels, Eric A., "Infectious Agents as Causes of Non-Hodgkin Lymphoma," Cancer Epidemiol Biomarkets Prev 2007, 16(3), Mar. 2007.
English Translation of Office Action issued for corresponding JP Patent Application No. 2010-543301, dated Aug. 13, 2013.
European Search Report issued from corresponding EP Application No. 11810446.2, dated Nov. 14, 2013.
European Search Report issued from corresponding European Patent Application No. 11810447.0, dated Feb. 18, 2014.
Examination Report issued in corresponding Australian Patent Application No. 2011280997, dated Aug. 14, 2014.

(56) References Cited

OTHER PUBLICATIONS

Examination Report issued in corresponding Australian Patent Application No. 2011281007, dated Aug. 7, 2014.
Examination Report issued in corresponding Australian Patent Application No. 2011281012, dated Aug. 7, 2014.
Examination Report issued in corresponding Australian Patent Application No. 2011280936, dated Aug. 7, 2014.
Examination Report issued in corresponding Australian Patent Application No. 2011280944, dated Jul. 26, 2014.
Examination Report issued in corresponding Australian Patent Application No. 2011281017, dated Aug. 7, 2014.
Examination Report issued in corresponding New Zealand Patent Application No. 602007, dated Feb. 26, 2014.
Examination Report issued in corresponding New Zealand Patent Application No. 607305, dated Jul. 2, 2013.
Examination Report issued in corresponding New Zealand Patent Application No. 621533, dated Feb. 26, 2014.
Examination Report issued in corresponding NZ Patent Application No. 703445, dated Jan. 22, 2015.
Examination Report issued in corresponding NZ Patent Application No. 703450, dated Jan. 22, 2015.
Examination Report received in corresponding New Zealand Application No. 711367, dated Sep. 9, 2015.
Examination Report relating to corresponding NZ Patent Application No. 586834, dated Feb. 24, 2011.
Extended European Search Report issued in corresponding European Application No. 11810453.8 dated Feb. 6, 2014.
Extended European Search Report issued in corresponding European Application No. 11810457.9 dated Dec. 4, 2013.
Extended European Search Report issued in corresponding European Application No. 11810461.1 dated Mar. 21, 2014.
Extended European Search Report issued in corresponding European Application No. 11810462.9 dated Dec. 13, 2013.
Extended European Search Report issued in corresponding European Application No. 11810464.5 dated Dec. 13, 2013.
Extended European Search Report relating to corresponding EP Application No. 09703015.9, dated Feb. 6, 2012.
Gautier, L., et al., "Affy-Analysis of Affymetrix GeneChip Data at the Probe Level," Bioinforrnatics, vol. 20, No. 3, 2004, pp. 307-315.
Ginos, M., et al., "Identification of a Gene Expression Signature Associate with Recurrent Disease in Squamous Cell Carcinoma of the Head and Neck," Cancer Research, 64, 55-63, Jan. 1, 2004.
Grigoriadis, et al., "Establishment of the Epithelial-Specific Transcriptome of Normal and Malignant Human Breast Cells Based on MPSS and Array Expression Data," Breast Cancer Research, vol. 8, No. 5, 1-15, 2006.
Guha, K.D., Scientisti Develope Novel Cancer Blood Test, The Harvard Crimson. Apr. 28, 2009, available via url: (thecrimson.com/article/2009/4/28/scientists-develop-novelcancer-blood-test!>.
Haakenson, Joshua et al. HDAC6 and Ovarian Cancer. Int. J. Mol. Sci. 2013, 14, 9514-9535.
Haupl et al.; Reactivation of Rheumatoid Arthritis After Pregnancy; Arthritis and Rheumatism. 2008. 58(10): 2981-2992.
Herwig, R., et al., "Ability of PSA-Positive Circulating Macrophages to Detect Prostate Cancer," The Prostate 32:290-298, 2005.
Herwig, R., et al., "Measurement of Intracellular Versus Extracellular Prostate-Specific Antigen Levels in Peripheral Macrophages: A New Approach to Noninvasive Diagnosis of Prostate Cancer," Clinical Prostate Cancer, vol. 3, No. 3, 184-188, 2004.
Holmgren, L., et al., "Horizontal Transfer of DNA by the Uptake of Apoptotic Bodies," Blood, vol. 93, No. 11 Jun. 1, 1999, pp. 3956-3963.
Office Action issued in corresponding IL Application No. 224321, dated Nov. 26, 2015.
Office Action issued in corresponding Israeli Application No. 207027 dated Jul. 23, 2014.
Office Action issued in corresponding Israeli Patent Application No. 224321, dated Dec. 28, 2014.
Office Action issued in corresponding Japanese Application No. 2013-521843, dated Sep. 8, 2015.
Office Action issued in corresponding Japanese Patent Application No. 2010-543301, dated Jul. 8, 2014.
Office Action issued in corresponding Japanese Patent Application No. 2014-025368, dated Jan. 27, 2015.
Office Action issued in corresponding Mexican Application No. MX/a/2013/000917, dated Oct. 13, 2015.
Office Action issued in corresponding Mexican Patent Application No. MX/a/2010/007822, dated Feb. 4, 2014.
Office Action issued in corresponding Mexican Patent Application No. MX/a/2010/007822, dated Oct. 14, 2014.
Office Action issued in corresponding New Zealand Patent Application No. 607304, dated Jul. 2, 2013.
Office Action issued in corresponding U.S. Appl. No. 12/836,191, dated Dec. 5, 2014.
Office Action issued in corresponding U.S. Appl. No. 13/188,683, dated Feb. 21, 2014.
Office Action issued in corresponding U.S. Appl. No. 13/188,964, dated Jul. 2, 2014.
Office Action issued in corresponding U.S. Appl. No. 13/349,670, dated Jul. 2, 2014.
Office Action issued in corresponding U.S. Appl. No. 13/836,191, dated May 8, 2014.
Office Action received in corresponding Chinese Application 201180046174.6, dated Apr. 17, 2015.
Office Action received in corresponding European Application 11810453.8, dated Apr. 29, 2015.
Office Action received in corresponding Mexican Application No. MX/a/2010/007822 dated Jun. 26, 2015.
Office Action received in corresponding South Korean Application 10-2010-7018216, dated Jun. 10, 2015.
Office Action received in corresponding Taiwanese Application 100126110, dated Apr. 24, 2015.
Office Action received in corresponding U.S. Appl. No. 13/811,682 dated Jul. 31, 2015.
Office Action received in corresponding U.S. Appl. No. 13/811,695 dated Aug. 3, 2015.
Office Action received in corresponding U.S. Appl. No. 13/811,701 dated Aug. 10, 2015.
Office Action received in corresponding U.S. Appl. No. 13/811,705 dated Aug. 10, 2015.
Office Action received in corresponding U.S. Appl. No. 13/811,706 dated Aug. 3, 2015.
Office Action relating to corresponding CA Application No. 2,712,303, dated Apr. 24, 2012.
Palmer, et al., "Cell-Type Specific Gene Expression Profiles of Leukocytes in Human Peripheral Blood," BMC Genomics, 2006,7:115.
Perou, C., et al., "Molecular Portraits of Human Breast Tumors," Nature, vol. 406, Aug. 17, 2000.
Powell, A. Harvard gazette. Apr. 20, 2009, available via url: news.harvard.edu/gazette/story/2009/04/hms-professor-devises-single- test-for-cancers/>.
Ransohoff, David F., "Bias as a Threat to the Validity of Cancer Molecular-Marker Research," Nature, vol. 5, Feb. 2005, 142-149.
Rogler, G. et al. Isolation and phenotypic characterization of colonic macrophages. Clin Exp Immunol 1998; 112:205-215.
Search Report and Written Opinion issued in corresponding Singapore Application No. 201300215-9, dated Nov. 17, 2015.
Search Report issued in corresponding Chinese Application No. 201180046174.6 dated Jan. 22, 2014.
Search Report issued in corresponding Eurasian Application No. 201390150 dated Jun. 20, 2013.
Segelmark, et al., "Autoimmune Kidney Diseases," Autoimmunity Reviews, 9 (2010) A366-A371.
Seo, J., et al., "Probe Set Algorithms: Is There a Rational Best Bet?" BMC Bioinformatics, 2006, 7:395.
Slonin, Donna K., "From Patterns to Pathways: Gene Expression Data Analysis Comes of Age," Nature Genetics Supplement, vol. 32, Dec. 2002.
Srivastava et al., The Inflammatory versus Constitutive Trafficking of Mononuclear Phagocytes into the Alveolar Space of Mice is Associated with Drastic Changes in Their Gene Expression Profiles; J Immunology. 2005. 175: 1884-1893.

(56) References Cited

OTHER PUBLICATIONS

Takahashi et al.; Gene expression profiling of clear cell renal cell carcinoma: Gene Identification and prognostic classificatio; PNAS vol. 98 No. 17 pp. 9754-9759 Aug. 14, 2001.
Taylor, Marcia L. et al. Flow Cytometric Analysis of Blood Monocytes and Alveolar Macrophages. Methods in Molecular Medicine, vol. 44: Asthma: Mechanisms and Protocols.
Thisted (1998) What is a P-Value. University of Chicago. May 25, 1998. accessed from http://www.stat.uchicago.edu/-thisted.six pages.
Tsuang et al.; Assessing the Validity of Blood-Based Gene Expression Profiles for the Classification of Schizophrenia and Bipolar Disorder: A Preliminary Report; American Journal of Medical Genetics Part B (Neuropsychiatic Genetics) 1338:1 2005).
Van't Veer, L., et al, "Expression Profiling Predicts Outcome in Breast Cancer," Breast Cancer Res., 20003, 5:57-58.
Webb, T. 2002 J Natl Cancer Inst 94:413-414.
West, et al., "Embracing the Complexity of Genomic Data for Personalized Medicine," Genome Research, 16:559-566, 2006.
Whitney, et al., "Individuality and Variation in Gene Expression Patterns in Human Blood," PNAS, Feb. 18, 2003, vol. 100, No. 4, 1896-1901.
Wu, Z., et al., "A Model Based Background Adjustment for Oligonucleotide Expression Arrays," Journal of the American Statistical Assoc., vol. 99, 909-917.
Yang et al.; Circumvention of Normal Constraints on Granule Protein Gene Expression in Peripheral Blood Neutrophils and Monocytes of Patients with Antineutrophil Cytoplastnic Autoantibody-Associated Glornerulonephritis; JAM Soc Nephrol vol. 15 pp. 2103-2114 2004.
Zakynthinos, Epaminondas et al. Inflammatory biomarkers in coronary artery disease. Journal of Cardiology (2009) 53, 317-333.
Zamora, et al., "The Hematologist," Scientific Psychic Poster, 2007.
Abravaya et al., "Detection of point mutations with a modified ligase chain reaction (Gap-LCR)," Nucleic Acids Res. 23:675-682 (1995).
Barany, "Genetic disease detection and DNA amplification using cloned thermostable ligase," Proc. Natl. Acad. Sci. USA 88:189-193 (1991).
Chiu et al., "Noninvasive prenatal diagnosis of fetal chromosomal aneuploidy by massively parallel genomic sequencing of DNA in maternal plasma," Proc Natl Acad Sci USA, 105:20458-20463 (2008).
Cohen et al., "Emerging technologies for sequencing antisense oligonucleotides: capillary electrophoresis and mass spectrometry," Adv. Chromatogr., 36:127-162 (1996).
Cotton et al., "Reactivity of cytosine and thymine in single-base-pair mismatches with hydroxylamine and osmium tetroxide and its application to the study of mutations," Proc. Natl. Acad. Sci., 85:4397-4401 (1988).
Cotton, "Current methods of mutation detection," Mutat. Res., 285:125-144 (1993).
Cronin et al., "Cystic fibrosis mutation detection by hybridization to light-generated DNA probe arrays," Human Mutation, 7:244-255 (1996).
Efron, "Empirical Bayes Estimates for Large-Scale Prediction Problems," J Am Stat Assoc, 104:1015-1028 (2009).
Gasparini et al., "Restriction site generating-polymerase chain reaction (RG—PCR) for the probeless detection of hidden genetic variation: application to the study of some common cystic fibrosis mutations," Mol. Cell Probes, 6:1-7 (1992).
Gibbs et al., "Detection of single DNA base differences by competitive oligonucleotide priming," Nucl. Acids Res., 17:2437-2438 (1989).
Griffin et al., "DNA sequencing. Recent innovations and future trends," Appl. Biochem. Biotechnol., 38:147-159 (1993).
Guatelli et al., "Isothermal, in vitro amplification of nucleic acids by a multienzyme reaction modeled after retroviral replication, " Proc. Natl. Acad. Sci. USA 87:1874-1878 (1990).
Hage et al., "Recent advances in chromatographic and electrophoretic methods for the study of drug-protein interactions," J. Chromatogr. B. Biomed. Sci. Appl., 12:499-525 (1997).
Hayashi, "PCR-SSCP: a method for detection of mutations," Genet. Anal. Tech. Appl., 9:73-79 (1992).
Heegaard, "Capillary electrophoresis for the study of affinity interactions," J. Mol. Recognit., 11 :141-148 (1998).
Hsu et al., "Detection of DNA point mutations with DNA mismatch repair enzymes," Carcinogenesis, 15:1657-1662 (1994).
Kang et al., "Adenoviral gene transfer of Caenorhabditis elegans n-3 fatty acid desaturase optimizes fatty acid composition in mammalian cells," Proc. Natl. Acad. Sci., 98:4050-4054 (2001).
Kang et al., "Essential fatty acid metabolism in cultured human airway epithelial cells," Biochim. Biophys. Acta., 1128:267-274 (1992).
Keen et al., "Rapid detection of single base mismatches as heteroduplexes on Hydrolink gels," Trends Genet., 7:5 (1991).
Kozal et al., "Extensive polymorphisms observed in HIV-1 Glade B protease gene using high-density oligonucleotide arrays," Nature Medicine, 2:753-759 (1996).
Kwoh et al., "Transcription-based amplification system and detection of amplified human immunodeficiency virus type 1 with a bead-based sandwich hybridization format," Proc. Natl. Acad. Sci. ,86:1173-1177 (1989).
Landegran et al., "A ligase-mediated gene detection technique," Science 241:1077-1080 (1988).
Li et al., "Replacing PCR with COLD-PCR enriches variant DNA sequences and redefines the sensitivity of genetic testing," Nat. Med. 14:579-584 (2008).
Lizardi et al. "Exponential amplification of recombinant—RNA hybridization probes," Bio/Technology 6:1197-1202 (1988).
Maxam et al., "A new method for sequencing DNA," Proc. Natl. Acad. Sci., 74:560-564 (1977).
Myers et al., "Detection of single base substitutions by ribonuclease cleavage at mismatches in RNA:DNA duplexes," Science, 230:1242-1246 (1985).
Myers et al., "Detection of single base substitutions in total genomic DNA," Nature, 313:495-498 (1985).
Naeve et al., "Accuracy of automated DNA sequencing: a multi-laboratory comparison of sequencing results," Ehotechniques 19:448-453 (1995).
Nakazawa et al., "UV and skin cancer: specific p53 gene mutation in normal skin as a biologically relevant exposure measurement," Proc. Natl. Acad. Sci., 91:360-364 (1994).
Orita et al., "Detection of polymorphisms of human DNA by gel electrophoresis as single-strand conformation polymorphisms," Proc. Natl. Acad. Sci., 86:2766-2770 (1989).
Prodromou et al., Recursive PCR: a novel technique for total gene synthesis, Protein Eng. 5:827-829(1992).
Prossner, "Detecting single-base mutations," Tibtech, 11:238-246 (1993).
Rivas et al., New developments in the study of biomolecular associations via sedimentation equilibrium, Trends Biochem. Sci., 18:284-287 (1993).
Rosenbaum et al. "Temperature-gradient gel electrophoresis. Thermodynamic analysis of nucleic acids and proteins in purified form and in cellular extracts". Biophys. Chem. 26, Elsevier 235-246 (1987).
Saiki et al., "Analysis of enzymatically amplified beta-globin and HLA-DQ alpha DNA with allele-specific oligonucleotide probes," Nature, 324:163-166 (1986).
Saiki et al., "Genetic analysis of amplified DNA with immobilized sequence-specific oligonucleotide probes," Proc. Natl. Acad. Sci. ,86:6230-6234 (1989).
Saleeba et al., "Chemical cleavage of mismatch to detect mutations," Methods Enzymol., 217:286-295 (1992).
Sanger et al., "DNA sequencing with chain-terminating inhibitors," Proc. Natl. Acad. Sci., 74:5463-5467 (1977).
Schiller et al., "Lipid analysis by matrix-assisted laser desorption and ionization mass spectrometry: A methodological approach," Anal. Biochem., 267:46-56 (1999).

(56) References Cited

OTHER PUBLICATIONS

Schiller et al., "Matrix-assisted laser desorption and ionization time-of-flight (MALDI-TOF) mass spectrometry in lipid and phospholipid research," Progress in Lipid Research, 43:449-488.
Sehnert et al., "Optimal detection of fetal chromosomal abnormalities by massively parallel DNA sequencing of cell-free fetal DNA from maternal blood," Clin Chem., 57:1042-1049 (2011).
Sjolander et al., Integrated fluid handling system for biomolecular interaction analysis, Anal. Chem. 63:2338-2345 (1991).
Szabo et al., "Surface plasmon resonance and its use in biomolecular interaction analysis (BIA)," Curr. Opin. Struct. Biol., 5:699-705 (1995).
Wachsman et al., "Noninvasive genomic detection of melanoma," Br J Dermatol., 164:797-806 (2011).
Weylandt et al., "Polyunsaturated fatty acids exert antiarrhythmic actions as free acids rather than in phospholipids," Lipids, 31:977-982 (1996).
Zaslona et al., Transcriptome profiling of primary murine monocytes, lung macrophages and lung dendritic cells reveals a distinct expression of genes involved in cell trafficking, Respiratory Research. Jan. 16, 2009. 10:2, pp. 1-16.
Zimmet et al: "Polyploidy: occurrence in nature, mechanisms, and significance for the megakaryocyte-platelet system", Experimental hematology, Jan. 1, 2000 (Jan. 1, 2000 ), pp. 3-16, XP055185388, Netherlands DOI: 10.1 016/S0301-472X(99)00124-1 Retrieved from the Internet: URL:http://www.ncbi.nlm.nih.gov/pubmed/1 0658672.
Arumugam et al., "S100P promotes pancreatic cancer growth, survival, and invasion." Clinical Cancer Research 11 (15):5356-5364 (2005).
Chaussable et al., "Unique gene expression profiles of human macrophages and dendritic cells to phylogenetically distinct parasites." Blood 102(2):672-681 (2003).
English Translation of Office Action issued in corresponding Chinese Patent Application No. 200980109695.4, dated Mar. 5, 2013.
Galati et al. "In vivo administration of GM-CSF promotes the clearance of apoptotic cells: effects on monocytes and polymorphonuclear leukocytes." Journal of Leukocyte Biology 67(2):174-182 (2000).
Gerna et al., "Comparative quantitation of human cytomegalovirus DNA in blood leukocytes and plasma of transplant and AIDS patients." Journal of Clinical Microbiology 32(11):2709-2717 (1994).
Henry et al., "Antigen-presenting cells that phagocytose apoptotic tumor-derived cells are potent tumor vaccines." Cancer Research 59(14):3329-3332 (1999).
Kagan et al., "Appetizing rancidity of apoptotic cells for macrophages: oxidation, externalization, and recognition of phosphatidylserine." American Journal of Physiology-Lung Cellular and Molecular Physiology 285(1)L1-L17 (2003).
Kavtsov et al., "Flow cytofluorometric assay of human whole blood leukocyte DNA degradation in response to Yersinia pestis and *Staphylococcus aureus*." Saratov Fall Meeting 2000: Optical Technologies in Biophysics and Medicine II. vol. 4241:260-267 International Society for Optics and Photonics (2001).
Kruger et al., "The additive effect of p53 Arg72Pro and RNASEL Arg462Gln genotypes on age of disease onset in Lynch syndrome patients with pathogenic germline mutations in MSH2 or MLH1." Cancer Letters 252(1):55-64 (2007).
Larson et al., "Apoptosis of circulating tumor cells in prostate cancer patients." Cytometry Part A 62(1):46-53 (2004).

Loubiere et al. "Maternal microchimerism in healthy adults in lymphocytes, monocyte/macrophages and NK cells." Laboratory Investigation 86(11):1185-1192 (2006).
Merdad et al., "Expression of matrix metalloproteinases (MMPs) in primary human breast cancer: MMP-9 as a potential biomarker for cancer invasion and metastasis." Anticancer Research 34(3):1355-1366 (2014).
Nagorsen et al., "Tumor-infiltrating macrophages and dendritic cells in human colorectal cancer; relation to local regulatory T cells, systemic T-cell response against tumor-associated antigens and survival," Journal of Translational Medicine 5:62 (2007).
Office Action issued for corresponding U.S. Appl. No. 12/836,191 dated Oct. 18, 2012.
Parekh et al., "Therapeutic targeting of the BCL6 oncogene for diffuse large B-cell lymphomas." Leukemia & Lymphoma 49(5):874-882 (2008).
Prasse et al., "IL-10-producing monocytes differentiate to alternatively activated macrophages and are increased in atopic patients." Journal of Allergy and Clinical Immunology 119(2):464-471 (2007).
Rennert et al., "An alternative spliced RNASEL variant in peripheral blood leukocytes." Journal of Interferon & Cytokine Research 26(11):820-826 (2006).
Stroun et al., "The origin and mechanism of circulating DNA." Annals of the New York Academy of Sciences 906(1):161-168 (2000).
Tang et al., "Gene expression in blood changes rapidly in neutrophils and monocytes after ischemic stroke in humans: a microarray study." Journal of Cerebral Blood Flow & Metabolism 26(8):1089-1102 (2006).
Jjam et al., "Isolation of monocytes from human peripheral blood using immuno-affinity expanded-bed adsorption." Biotechnology and Bioengineering 83(5):554-566 (2003).
Zaslona et al., "Transcriptome profiling of primary murine monocytes, lung macrophages and lung dendritic cells reveals a distinct expression of genes involved in cell trafficking." Respiratory Research 10(2):1-16 (2009).
Zimmet et al., "Polyploidy: occurrence in nature, mechanisms, and significance for the megakaryocyte-platelet system." Experimental Hematology 28(1):3-16 (2000).
Affyrnetrix Show Results printout. Search query BAK1 against HG-U133 Plus 2 microarray. Obtained from https://www.affymetrix.com/analysis/netaffx/showresults.affx on Nov. 1, 2019. One page. (Year: 2019).
Affymetrix Show Results printout. Search query EGFR against HG-U133 Plus 2 microarray. Obtained from https://www.affymetrix.com/analysis/netaffx/showresults.affx on Nov. 1, 2019. One page. (Year: 2019).
Affyrnetrix Show Results printout. Search query ERBB2 against HG-U133 Plus 2 microarray. Obtained from https://www.affymetrix.com/analysis/netaffx/showresults.affx on Nov. 1, 2019. Two pages. (Year: 2019).
De Visser et al., "Paradoxical roles of the immune system during cancer development." Nature Reviews Cancer 6(1):24-37 (2006).
Shields et al. "10 new mammals discovered in past 10 years." The Guardian [Retrieved Jul. 12, 2019] <https://www.theguardian.com/environment/2012/sep/13/new-mammals-discovered-10-years> (2012).
Vankayalapati et al. "The NKp46 Receptor Contributes to NK Cell Lysis of Mononuclear Phagocytes Infected with an Intracellular Bacterium." The Journal of Immunology 168(7): 3451-3457 (2002).

\* cited by examiner

Phagocytic WBC (e.g., macrophage)

n = 2 n > 2

METHODS OF DETECTING AUTOIMMUNE OR IMMUNE-RELATED DISEASES OR CONDITIONS

RELATED APPLICATION DATA

This application is a continuation application which claims priority to U.S. patent application Ser. No. 13/811,695, filed on Apr. 4, 2013, which is a National Stage Application under 35 U.S.C. 371 of co-pending PCT application PCT/US2011/044973 designating the United States and filed Jul. 22, 2011; which claims the benefit of U.S. provisional patent application No. 61/367,018 and filed Jul. 23, 2010 each of which are hereby incorporated by reference in their entireties.

FIELD OF THE INVENTION

This invention relates generally to methods of using phagocytic cells alone or in combination with non-phagocytic cells in the diagnosis, prognosis, or monitoring of autoimmune or immune-related diseases or conditions. The invention also relates to methods of using phagocytic cells alone or in combination with non-phagocytic cells to identify markers of autoimmune or immune-related diseases or conditions.

BACKGROUND OF THE INVENTION

Early diagnosis of a disease often increases the likelihood of successful treatment or cure of such disease. Current diagnostic methods, however, depend largely on population-derived average values obtained from healthy individuals. Personalized diagnostic methods are needed that enable the diagnosis, especially the early diagnosis, of the presence of a disease or a condition in individuals who are not known to have the disease or who have recurrent disease. This is of particular importance in autoimmune or immune-related diseases or conditions, which affect over 23.5 million Americans.

Leukocytes begin as pluripotent hematopoietic stem cells in the bone marrow and develop along either the myeloid lineage (monocytes, macrophages, neutrophils, eosinophils, and basophils) or the lymphoid lineage (T and B lymphocytes and natural killer cells). The major function of the myeloid lineage cells (e.g., neutrophils and macrophages) is the phagocytosis of infectious organisms, live unwanted damaged cells, senescent and dead cells (apoptotic and necrotic), as well as the clearing of cellular debris. Phagocytes from healthy animals do not replicate and are diploid, i.e., have a DNA index of one. On average, each cell contains <10 ng DNA, <20 ng RNA, and <300 ng of protein.

One object of the present invention is to provide diagnostic methods that can facilitate the detection of autoimmune or immune-related disease or condition-specific markers, e.g., nucleic acids, proteins, carbohydrates, and/or lipids and the like by using phagocytic cells alone, or in combination with non-phagocytic cells. Another object of this invention is to provide methods of identifying autoimmune or immune-related disease or condition-specific markers and further use such markers alone or together with any known markers to diagnose diseases or conditions.

SUMMARY OF THE INVENTION

We have invented new and useful methods for detecting/diagnosing autoimmune or immune-related diseases or conditions by using phagocytic cells alone or in combination with non-phagocytic cells. In some embodiments, phagocytic cells serve as surrogates for diseased cells and non-phagocytic cells serve as control cells. In other embodiments, two sub-populations of phagocytic cells are used, wherein the phagocytic cells that have a DNA content greater than 2n (the >2n phagocytic cells) serve as surrogates for diseased cells, while the phagocytic cells that have a DNA content of 2n (the =2n phagocytic cells) serve as control cells.

In one aspect, this invention provides a method for diagnosing or aiding in the diagnosis of an autoimmune or immune-related disease or condition in a subject comprising: a) determining a first profile of one or more markers of the disease or condition from a population of phagocytic cells; b) determining a second profile of at least one of the one or more markers from a population of non-phagocytic cells; and c) identifying a difference between the first and second profiles of at least one or more of said markers, wherein the difference is indicative of the presence of said disease or condition in the subject.

In another aspect, this invention provides a method for assessing the risk of developing an autoimmune or immune-related disease or condition in a subject comprising: a) determining a first profile of one or more markers of the disease or condition from a population of phagocytic cells; b) determining a second profile of at least one of the one or more markers from a population of non-phagocytic cells; and c) identifying a difference between the first and second profiles of at least one or more of said markers, wherein the difference is indicative of the risk of developing said disease or condition in the subject.

In yet another aspect, this invention provides a method for prognosing or aiding in the prognosis of an autoimmune or immune-related disease or condition in a subject comprising: a) determining a first profile of one or more markers of the disease or condition from a population of phagocytic cells; b) determining a second profile of at least one of the one or more markers from a population of non-phagocytic cells; and c) identifying a difference between the first and second profiles of at least one or more of said markers, wherein the identified difference is indicative of the prognosis of said disease or condition in the subject.

In yet another aspect, this invention provides a method for assessing the efficacy of a treatment for an autoimmune or immune-related disease or condition in a subject comprising: a) determining a first profile of one or more markers of the disease or condition from a population of phagocytic cells from the subject before the treatment; determining a second profile of at least one of the one or more markers from a population of non-phagocytic cells from the subject before the treatment; identifying a first difference between the first and second profiles of at least one or more of said markers; b) determining a third profile of the one or more markers from a population of phagocytic cells from the subject after the treatment; determining a fourth profile of at least one of the one or more markers from a population of non-phagocytic cells from the subject after the treatment; identifying a second difference between the third and fourth profiles of at least one or more of said markers; and c) identifying a difference between the first difference and the second difference, wherein the identified difference is indicative of the efficacy of the treatment for said disease or condition in the subject.

In yet another aspect, this invention provides a method for monitoring the progression or regression of an autoimmune or immune-related disease or condition in a subject comprising: a) determining a first profile of one or more markers of the disease or condition from a population of phagocytic cells from the subject at a first time point; determining a second profile of at least one of the one or more markers from a population of non-phagocytic cells from the subject at the first time point; identifying a first difference between the first and second profiles of at least one or more of said markers; b) determining a third profile of the one or more markers from a population of phagocytic cells from the subject at a second time point; determining a fourth profile of at least one of the one or more markers from a population of non-phagocytic cells from the subject at the second time point; identifying a second difference between the third and fourth profiles of at least one or more of said markers; and c) identifying a difference between the first difference and the second difference, wherein the identified difference is indicative of the progression or regression of said disease or condition in the subject.

In yet another aspect, this invention provides a method for identifying a compound capable of ameliorating or treating an autoimmune or immune-related disease or condition in a subject comprising: a) determining a first profile of one or more markers of the disease or condition from a population of phagocytic cells from the subject before administering the compound to the subject; determining a second profile of at least one of the one or more markers from a population of non-phagocytic cells from the subject before administering the compound to the subject; identifying a first difference between the first and second profiles of at least one or more of said markers; b) determining a third profile of the one or more markers from a population of phagocytic cells from the subject after the administration of the compound; determining a fourth profile of at least one of the one or more markers from a population of non-phagocytic cells from the subject after the administration of the compound; identifying a second difference between the third and fourth profiles of at least one or more of said markers; and c) identifying a difference between the first difference and the second difference, wherein the identified difference indicates that the compound is capable of ameliorating or treating said disease or condition in the subject.

In yet another aspect, this invention provides a method for diagnosing or aiding in the diagnosis of an autoimmune or immune-related disease or condition in a subject comprising: a) determining a first profile of one or more markers of the disease or condition from a population of phagocytic cells having a DNA content more than 2n ($>2n$ phagocytic cells); b) determining a second profile of at least one of the one or more markers from a population of phagocytic cells having a DNA content of 2n ($=2n$ phagocytic cells); and c) identifying a difference between the first and second profiles of at least one or more of said markers, wherein the difference is indicative of the presence of said disease or condition in the subject.

In yet another aspect, this invention provides a method for assessing the risk of developing an autoimmune or immune-related disease or condition in a subject comprising: a) determining a first profile of one or more markers of the disease or condition from a population of $>2n$ phagocytic cells; b) determining a second profile of at least one of the one or more markers from a population of $=2n$ phagocytic cells; and c) identifying a difference between the first and second profiles of at least one or more of said markers, wherein the difference is indicative of the risk of developing said disease or condition in the subject.

In yet another aspect, this invention provides a method for prognosing or aiding in the prognosis of an autoimmune or immune-related disease or condition in a subject comprising: a) determining a first profile of one or more markers of the disease or condition from a population of $>2n$ phagocytic cells; b) determining a second profile of at least one of the one or more markers from a population of $=2n$ phagocytic cells; and c) identifying a difference between the first and second profiles of at least one or more of said markers, wherein the difference is indicative of the prognosis of said disease or condition in the subject.

In yet another aspect, this invention provides a method for assessing the efficacy of a treatment for an autoimmune or immune-related disease or condition in a subject comprising: a) determining a first profile of one or more markers of the disease or condition from a population of $>2n$ phagocytic cells from the subject before the treatment; determining a second profile of at least one of the one or more markers from a population of $=2n$ phagocytic cells from the subject before the treatment; identifying a first difference between the first and second profiles of at least one or more of said markers; b) determining a third profile of the one or more markers from a population of $>2n$ phagocytic cells from the subject after the treatment; determining a fourth profile of at least one of the one or more markers from a population of $=2n$ phagocytic cells from the subject after the treatment; identifying a second difference between the third and fourth profiles of at least one or more of said markers; and c) identifying a difference between the first difference and the second difference, wherein the identified difference is indicative of the efficacy of the treatment for said disease or condition in the subject.

In yet another aspect, this invention provides a method for monitoring the progression or regression of an autoimmune or immune-related disease or condition in a subject comprising: a) determining a first profile of one or more markers of the disease or condition from a population of $>2n$ phagocytic cells from the subject at a first time point; determining a second profile of at least one of the one or more markers from a population of $=2n$ phagocytic cells from the subject at the first time point; identifying a first difference between the first and second profiles of at least one or more of said markers; b) determining a third profile of the one or more markers from a population of $>2n$ phagocytic cells from the subject at a second time point; determining a fourth profile of at least one of the one or more markers from a population of $=2n$ phagocytic cells from the subject at the second time point; identifying a second difference between the third and fourth profiles of at least one or more of said markers; and c) identifying a difference between the first difference and the second difference, wherein the identified difference is indicative of the progression or regression of said disease or condition in the subject.

In yet another aspect, this invention provides a method for identifying a compound capable of ameliorating or treating an autoimmune or immune-related disease or condition in a subject comprising: a) determining a first profile of one or more markers of the disease or condition from a population of $>2n$ phagocytic cells from the subject before administering the compound to the subject; determining a second profile of at least one of the one or more markers from a population of $=2n$ phagocytic cells from the subject before administering the compound to the subject; identifying a first difference between the first and second profiles of at least one or more of said markers; b) determining a third profile of the one or more markers from a population of $>2n$ phagocytic cells from the subject after the administration of the compound; determining a fourth profile of at least one of the one or more markers from a population of =2n phagocytic cells from the subject after the administration of the compound; identifying a second difference between the third and fourth profiles of at least one or more of said markers; c) identifying a difference between the first difference and the second difference, wherein the identified difference indicates that the compound is capable of ameliorating or treating said disease or condition in the subject.

In yet another aspect, this invention provides a method for identifying one or more markers for an autoimmune or immune-related disease or condition comprising: a) determining a first profile of analytes from phagocytic cells from a subject having said disease or condition; determining a second profile of analytes from non-phagocytic cells from the subject having said disease or condition; identifying a first set of differences between the first and second profiles, wherein the first set of differences is specific to the first profile relative to the second profile; b) determining a third profile of analytes from phagocytic cells from a control subject not having said disease or condition; determining a fourth profile of analytes from non-phagocytic cells from the control subject not having said disease or condition; identifying a second set of differences between the third and fourth profiles, wherein the second set of differences is specific to the third profile relative to the fourth profile; c) identifying one or more analytes specific to the first set of differences relative to the second set of differences, the identified analytes being markers of said disease or condition. Optionally, this method further comprises d) obtaining a fifth profile of analytes from cells or tissues affected by said disease or condition in the subject having said disease or condition; obtaining a sixth profile of analytes from cells or tissues not affected by said disease or condition in the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comparison: a) determining a first profile of analytes from phagocytic cells from a subject having said disease or condition; determining a second profile of analytes from phagocytic cells from a control subject not having said disease or condition; identifying a first set of differences between the first and second profiles, wherein the first set of differences is specific to the first profile relative to the second profile; b) determining a third profile of analytes from non-phagocytic cells from the subject having said disease or condition; determining a fourth profile of analytes from non-phagocytic cells from the control subject not having said disease or condition; identifying a second set of differences between the third and fourth profiles, wherein the second set of differences is specific to the third profile relative to the fourth profile; c) identifying one or more analytes specific to the first set of differences relative to the second set of differences, the identified analytes being markers of said disease or condition. And optionally, the method further comprises d) obtaining a fifth profile of analytes from cells or tissues affected by said disease or condition in the subject having said disease or condition; obtaining a sixth profile of analytes from cells or tissues not affected by said disease or condition in the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comprising: a) determining a first profile of analytes from phagocytic cells from a subject having said disease or condition; obtaining a second profile of analytes from phagocytic cells from a control subject not having said disease or condition by data mining; identifying a first set of differences between the first and second profiles, wherein the first set of differences is specific to the first profile relative to the second profile; b) determining a third profile of analytes from non-phagocytic cells from the subject having said disease or condition; obtaining a fourth profile of analytes from non-phagocytic cells from a control subject not having said disease or condition by data mining; identifying a second set of differences between the third and fourth profiles, wherein the second set of differences is specific to the third profile relative to the fourth profile; and c) identifying one or more analytes specific to the first set of differences relative to the second set of differences, the identified analytes being markers of said disease or condition. And optionally, the method further comprises d) obtaining a fifth profile of analytes from cells or tissues affected by said disease or condition by data mining; obtaining a sixth profile of analytes from cells or tissues not affected by said disease or condition by data mining; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comprising: a) determining a first profile of analytes from phagocytic cells from a subject having said disease or condition; determining a second profile of analytes from non-phagocytic cells from the subject having said disease or condition; identifying a first set of differences between the first and second profiles, wherein the first set of differences is specific to the first profile relative to the second profile; b) determining a third profile of analytes from cells or tissues affected by said disease or condition from the subject having said disease or condition; determining a fourth profile of analytes from cells or tissues not affected by said disease or condition from the subject having said disease or condition; identifying a second set of differences between the third and fourth profiles, wherein the second set of differences is specific to the third profile relative to the fourth profile; c) identifying one or more analytes present in both the first set of differences and the second set of differences, the identified analytes being markers of said disease or condition. And optionally, the method further comprises d) determining a fifth profile of analytes from phagocytic cells from a control subject not having said disease or condition; identifying a third set of differences between the first and fifth profiles, wherein the third set of differences is specific to the first profile relative to the fifth profile; e) identifying at least one of the one or more markers of c) present in the third set of differences.

In yet another aspect, this invention provides a method for identifying one or more markers of an autoimmune or immune-related disease or condition comprising: a) determining a first profile of analytes from >2n phagocytic cells from a subject having said disease or condition; determining a second profile of analytes from =2n phagocytic cells from the subject having said disease or condition; identifying a first set of differences between the first and second profiles, wherein the first set of differences is specific to the first profile relative to the second profile; b) determining a third profile of analytes from >2n phagocytic cells from a control subject not having said disease or condition; determining a fourth profile of analytes from =2n phagocytic cells from the control subject not having said disease or condition; identifying a second set of differences between the third and fourth profiles, wherein the second set of differences is specific to the third profile relative to the fourth profile; and c) identifying one or more analytes specific to the first set of differences relative to the second set of differences, the identified analytes being markers of said disease or condition. And optionally, the method further comprises: d) obtaining a fifth profile of analytes from cells or tissues affected by said disease or condition from the subject having said disease or condition; obtaining a sixth profile of analytes from cells or tissues not affected by said disease or condition from the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

In some embodiments, the markers or the analytes are nucleic acids (e.g., nucleotides, oligonucleotides, DNAs, RNAs, or DNA-RNA hybrids), proteins (e.g., amino acids, peptides, enzymes, antigens, antibodies, cytokines, lipoproteins, glycoproteins, or hormones), lipids (e.g., fatty acids, phosphatides, cholesterol), carbohydrates (e.g., monosaccharides, disaccharides, polysaccharides), metabolites (e.g., vitamins, primary metabolites, secondary metabolites), or combinations thereof.

In some embodiments, the profile is a nucleic acid profile (e.g., genotypic profile, a single nucleotide polymorphism profile, a gene mutation profile, a gene copy number profile, a DNA methylation profile, a DNA acetylation profile, a chromosome dosage profile, a gene expression profile), a protein profile (e.g., protein expression, protein activation), a lipid profile, a carbohydrate profile, a metabolite profile, or a combination thereof. In some embodiments, the profile is determined by a qualitative assay, a quantitative assay, or a combination thereof.

In some embodiments, at least one of the one or more markers is up-regulated or activated in the phagocytic cells compared to the non-phagocytic cells. In some embodiments, at least one of the one or more markers is down-regulated or inhibited in the phagocytic cells compared to the non-phagocytic cells. In some embodiments, at least one of the one or more markers is up-regulated or activated in the >2n phagocytic cells compared to the =2n phagocytic cells. In some embodiments, at least one of the one or more markers is down-regulated or inhibited in the >2n phagocytic cells compared to the =2n phagocytic cells.

In some embodiments, the first profile, the second profile, the third profile, the fourth profile, the fifth profile, or the sixth profile comprises the absence of at least one of the one or more markers.

In some embodiments, the difference is at least 1.05-fold, 1.1-fold, 1.2-fold, 1.3-fold, 1.4-fold, 1.5-fold, 2-fold, 2.5-fold, 3-fold, 4-fold, 5-fold, 6-fold, 7-fold, 8-fold, 9-fold, or 10-fold difference.

In some embodiments, the methods of this invention also comprise lysing the phagocytic cells (e.g., >2n phagocytic cells, or =2n phagocytic cells), and the non-phagocytic cells; and also extracting the cellular contents from those cells. In some embodiments, the cellular contents of the phagocytic cells comprise viable diseased cells, dead diseased cells, apoptotic diseased cells, circulating tumor cells, infectious agents, fetal cells, trophoblasts, or fragments thereof. In some embodiments, the cellular contents of the >2n phagocytic cells comprise viable diseased cells, dead diseased cells, apoptotic diseased cells, circulating tumor cells, infectious agents, fetal cells, trophoblasts, or fragments thereof.

In some embodiments, at least one of the one or more markers of the disease or condition is present in the cellular contents of the phagocytic cells. In some embodiments, the one or more markers of said disease or condition are not present in the cellular contents of the non phagocytic cells. In some embodiments, the phagocytic cells express at least one of the one or more markers of said disease or condition.

In some embodiments, at least one of the one or more markers of the disease or condition is present in the cellular contents of the >2n phagocytic cells. In some embodiments, the one or more markers of said disease or condition are not present in the cellular contents of the =2n phagocytic cells. In some embodiments, the phagocytic cells express at least one of the one or more markers of said disease or condition. In some embodiments, the >2n phagocytic cells express at least one of the one or more markers of said disease or condition.

In some embodiments, the methods of this invention also comprise comparing the identified difference of c) to a repository of one or more known markers of said disease or condition (e.g., data obtained by data mining).

In some embodiments, the phagocytic cells are professional phagocytic cells (e.g., neutrophils, macrophages, monocytes, dendritic cells, foam cells, mast cells, eosinophils), non-professional phagocytic cells (e.g., epithelial cells, endothelial cells, fibroblasts, mesenchymal cells), or mixtures thereof. In some embodiments, the non-phagocytic cells are T cells, B cells, null cells, basophils, or mixtures thereof.

In some embodiments, the phagocytic cells (e.g., >2n phagocytic cells, =2n phagocytic cells) and the non-phagocytic cells are isolated from a bodily fluid sample (e.g., blood, urine), tissues, or cells (e.g., white blood cells, fetal cells) of the subject.

In some embodiments, a standard/know cell separation/isolation/purification technique, such as antibody, flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platforms, or a combination thereof, is used to isolate phagocytic cells (e.g., >2n phagocytic cells and =2n phagocytic cells) and non-phagocytic cells from bodily fluids, tissues or cells, or to separate phagocytic cells from non-phagocytic cells, or to separate >2n phagocytic cells from =2n phagocytic cells. In some embodiments, the phagocytic cells (e.g., >2n phagocytic cells) can also be isolated by using a product secreted by the phagocytic cells, or by using a cell surface target (e.g., a receptor protein, a marker of said disease or condition) on the surface of the phagocytic cells. In some embodiments, the target is expressed by the phagocytic cells. In other embodiments, the target is not expressed by the phagocytic cells. In some embodiments, the phagocytic cells (e.g., >2n phagocytic cells and =2n phagocytic cells) and the non-phagocytic cells are isolated using a ligand that binds to a molecular receptor expressed on the plasma membranes of white blood cells.

Also provided by this invention are markers that can be used in the methods of this invention and that can be identified by the methods of this invention.

DETAILED DESCRIPTION OF THE INVENTION

Figure 1A:
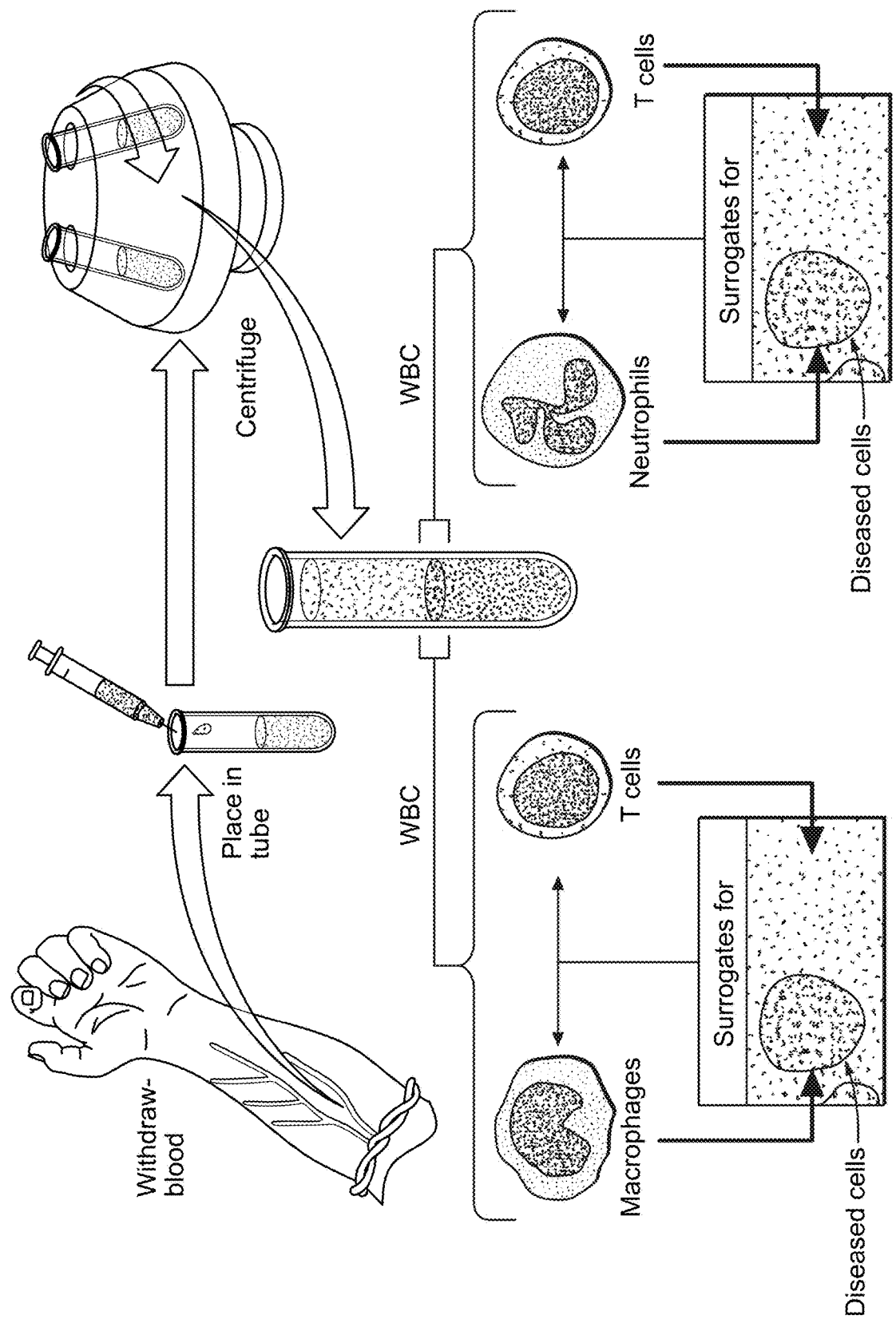
FIG. 1A schematically depicts one embodiment of a method of the invention for diagnosing or aiding in the diagnosis of an autoimmune or immune-related disease or condition. In this embodiment, phagocytic cells and non-phagocytic cells are separated from white blood cells of a subject. The phagocytic cells serve as surrogates for diseased cells, while the non-phagocytic cells serve as control cells.
Figure 1B:
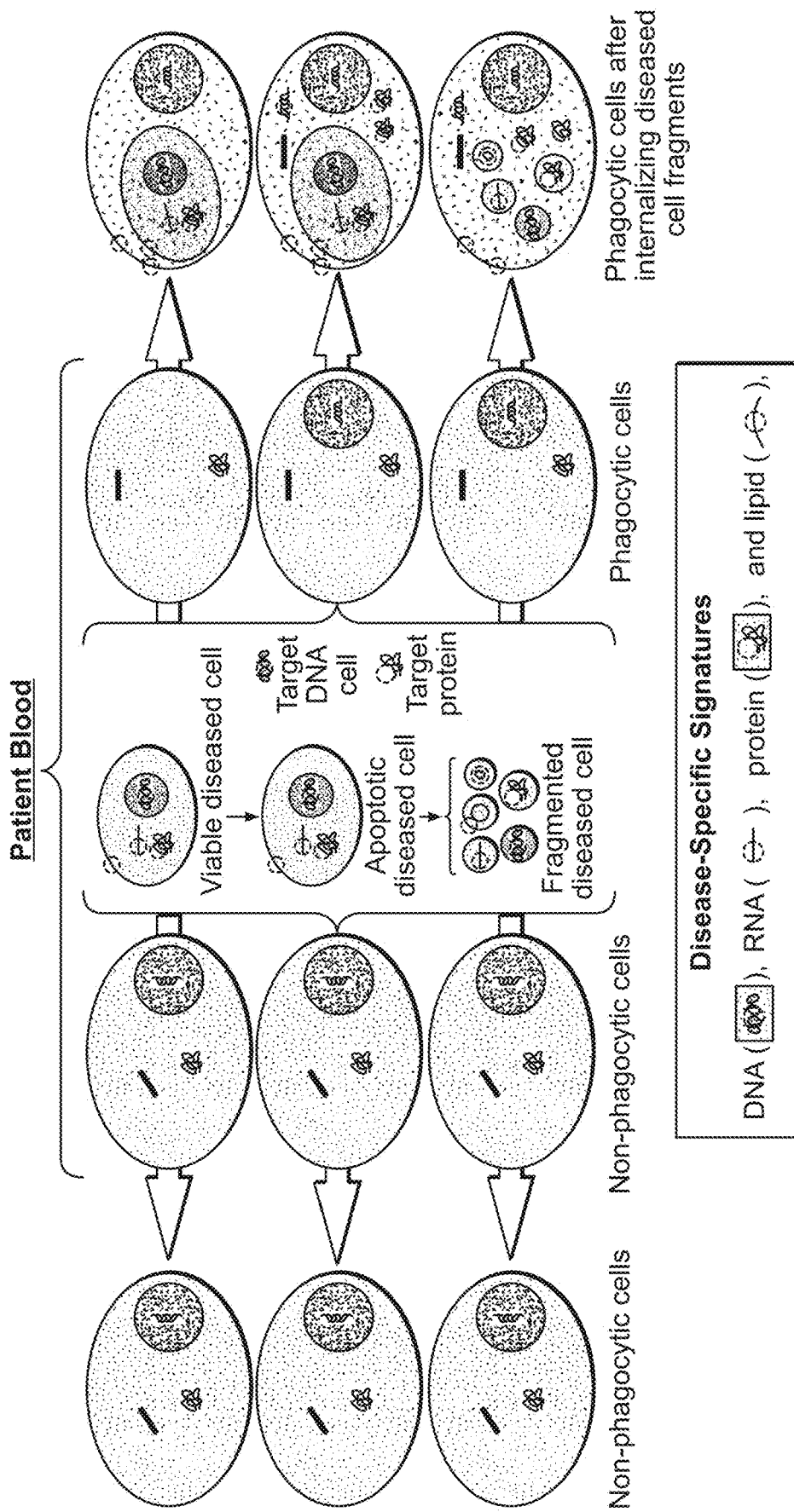
FIG. 1B schematically depicts one proposed pathway leading to acquisition of an autoimmune or immune-related disease-specific DNA, RNA, protein and/or lipid markers by phagocytic cells. Blood phagocytes engulf viable circulating diseased cells, apoptotic diseased cells, and/or fragmented diseased cells. Accordingly, the disease-specific markers (e.g., DNAs, RNAs, proteins, or lipids) that are contained within these diseased cells/fragments are also internalized by phagocytic cells. By contrast, non-phagocytic cells do not internalize these diseased cells/fragments, and, therefore, do not contain and/or express the disease-specific markers.

Unless otherwise defined herein, scientific and technical terms used in this application shall have the meanings that are commonly understood by those of ordinary skill in the art. Generally, nomenclature used in connection with, and techniques of, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

A "patient", "subject", or "individual" are used interchangeably and refer to either a human or a non-human animal. These terms include mammals, such as humans, primates, livestock animals (e.g., bovines, porcines), companion animals (e.g., canines, felines) and rodents (e.g., mice and rats).

As used herein, a control subject refers to any individual that has not been diagnosed as having the disease or condition being assayed. The terms "normal control", "healthy control", and "not-diseased cells" likewise mean a sample (e.g., cells, serum, tissue) taken from a source (e.g., subject, control subject, cell line) that does not have the condition or disease being assayed and therefore may be used to determine the baseline for the condition or disorder being measured. It is also understood that the control subject, normal control, and healthy control, include data obtained and used as a standard, i.e. it can be used over and over again for multiple different subjects. In other words, for example, when comparing a subject sample to a control sample, the data from the control sample could have been obtained in a different set of experiments, for example, it could be an average obtained from a number of healthy subjects and not actually obtained at the time the data for the subject was obtained.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, e.g., a marker, the presence, absence, amount, or change in amount of which is indicative of the presence, severity, or absence of the condition.

The term "prognosis" as used herein refers to is used herein to refer to the likelihood of an autoimmune or immune-related disease or condition progression, including recurrence of a disease or condition.

The disclosure of the International Application PCT/US2009/031395 is incorporated herein by reference for all purposes.

DESCRIPTION OF METHODS OF THE INVENTION

The present invention provides methods for diagnosing or aiding in the diagnosis of an autoimmune or immune-related disease or condition by comparing profiles (e.g., gene/protein/lipid/carbohydrate expression profiles, genotypes, gene copy number, gene dosage, DNA methylation, etc.) of disease or condition-associated markers (e.g., nucleic acids, proteins, lipids, carbohydrates, metabolites) between phagocytic cells having different DNA contents (>2n vs. =2n) taken from the same individual, or between phagocytic cells and non-phagocytic cells taken from the same individual.

This invention also provides methods for assessing the risk of developing an autoimmune or immune-related disease or condition, prognosing said disease, monitoring said disease progression or regression, assessing the efficacy of a treatment, or identifying a compound capable of ameliorating or treating said disease or condition.

Such a subject-specific profile comparison eliminates the dependence on a population-derived average profile for a particular disease or condition, which may introduce error into the detection or diagnosis of a particular disease or condition in the subject. The methods of this invention allow detection, diagnosis, and treatment to be personalized to the individual.

The methods of this invention (i) have high specificity, sensitivity, and accuracy and are capable of detecting disease or condition-specific markers present within a bodily fluid sample, cells or tissues; and (ii) eliminate the "inequality of baseline" that is known to occur among individuals due to intrinsic (e.g., age, gender, ethnic background, health status and the like) and temporal variations in marker expression. Accordingly, in certain aspects, the invention provides non-invasive assays for the early detection of a disease or condition, i.e., before the disease can be diagnosed by conventional diagnostic techniques, e.g., imaging techniques, and, therefore, provide a foundation for improved decision-making relative to the needs and strategies for intervention, prevention, and treatment of individuals with such disease or condition.

The methods of this invention can be used together with any known diagnostic methods, such as physical inspection, visual inspection, biopsy, scanning, histology, radiology, imaging, ultrasound, use of a commercial kit, genetic testing, immunological testing, analysis of bodily fluids, or monitoring neural activity.

Phagocytic cells that can be used in the methods of this invention include all types of cells that are capable of ingesting various types of substances (e.g., apoptotic cells, infectious agents, dead cells, viable cells, cell-free DNAs, cell-free RNAs, cell-free proteins). In some embodiments, the phagocytic cells are professional phagocytic cells, such as neutrophils, macrophages, monocytes, dendritic cells, foam cells, mast cells, or eosinophils. In some embodiments, the phagocytic cells are non-professional phagocytic cells, such as epithelial cells, endothelial cells, fibroblasts, or mesenchymal cells. In other embodiments, the phagocytic cells can be a mixture of different types of phagocytic cells. Non-phagocytic cells that can be used in this invention include, but are not limited to, T cells, B cells, null cells, basophils, or mixtures thereof.

As used herein, "the >2n phagocytic cells" refer to phagocytic cells that have a DNA content of greater than 2n, while "the =2n phagocytic cells" refer to phagocytic cells that have a DNA content of 2n. According to the present invention, some phagocytic cells engulf live/dying/dead diseased cells (and sub-cellular fragments thereof) and/or cell-free disease-specific nucleic acids, proteins, carbohydrates and/or lipids present in bodily fluids. Such phagocytosis leads to the internalization of these disease markers into the phagocytic cell and, therefore, the DNA content of these phagocytic cells will become greater than 2n. By contrast, some phagocytic cells have not engulfed living/dying/dead diseased cells or fragments and/or cell-free disease-specific nucleic acids, proteins, lipids, and/or carbohydrates present in bodily fluids. The DNA contents of this group of phagocytic cells remain 2n. In some embodiments, the disease-specific markers (e.g., DNA with disease-specific mutations) can be expressed by the >2n phagocytic cells. For example, the mutated DNA of diseased cells is integrated into the normal DNA of the >2n phagocytic cells. The subsequent transcription of the "integrated" DNA of the >2n phagocytic cells into RNA and the translation of the latter into proteins produces a phenotype different from the phagocytic cells that have not phagocytosed the diseased cells (i.e., the =2n phagocytic cells). In other embodiments, the internalized disease-specific markers are not expressed by the >2n phagocytic cells. The markers may be translocated onto the membranes of the >2n phagocytic cells, or secreted out by the >2n phagocytic cells.

As used herein, a "profile" of a marker of a disease or condition can broadly refer to any information concerning the marker. This information can be either qualitative (e.g., presence or absence) or quantitative (e.g., levels, copy numbers, or dosages). In some embodiments, a profile of a marker can indicate the absence of this marker. The profile can be a nucleic acid (e.g., DNA or RNA) profile, a protein profile, a lipid profile, a carbohydrate profile, a metabolite profile, or a combination thereof. A "marker" as used herein generally refers to an analyte which is differentially detectable in phagocytes and is indicative of the presence of a disease or condition. An analyte is differentially detectable if it can be distinguished quantitatively or qualitatively in phagocytes.

The methods of this invention can be applied to various autoimmune or immune-related diseases or conditions. As used herein, "autoimmune or immune-related disease or condition" can refer to any disease, disorder, or condition affecting or associated with the immune system. Examples of autoimmune or immune-related diseases or conditions include, but are not limited to, inflammation, antiphospholipid syndrome, systemic lupus erythematosus, rheumatoid arthritis, autoimmune vasculitis, celiac disease, autoimmune thyroiditis, post-transfusion immunization, maternal-fetal incompatibility, transfusion reactions, immunological deficiency such IgA deficiency, common variable immunodeficiency, drug-induced lupus, diabetes mellitus, Type I diabetes, Type II diabetes, juvenile onset diabetes, juvenile rheumatoid arthritis, psoriatic arthritis, multiple sclerosis, immunodeficiency, allergies, asthma, psoriasis, atopic dermatitis, allergic contact dermatitis, chronic skin diseases, amyotrophic lateral sclerosis, chemotherapy-induced injury, graft-vs-host diseases, bone marrow transplant rejection, Ankylosing spondylitis, atopic eczema, Pemphigus, Behcet's disease, chronic fatigue syndrome fibromyalgia, chemotherapy-induced injury, myasthenia gravis, glomerulonephritis, allergic retinitis, systemic sclerosis, subacute cutaneous lupus erythematosus, cutaneous lupus erythematosus including chilblain lupus erythematosus, Sjogren's syndrome, autoimmune nephritis, autoimmune vasculitis, autoimmune hepatitis, autoimmune carditis, autoimmune encephalitis, autoimmune mediated hematological diseases, lc-SSc (limited cutaneous form of scleroderma), dc-SSc (diffused cutaneous form of scleroderma), autoimmune thyroiditis (AT), Grave's disease (GD), myasthenia gravis, multiple sclerosis (MS), ankylosing spondylitis, transplant rejection, immune aging, rheumatic/autoimmune diseases, mixed connective tissue disease, spondyloarthropathy, psoriasis, psoriatic arthritis, myositis, scleroderma, dermatomyositis, autoimmune vasculitis, mixed connective tissue disease, idiopathic thrombocytopenic purpura, Crohn's disease, human adjuvant disease, osteoarthritis, juvenile chronic arthritis, a spondyloarthropathy, an idiopathic inflammatory myopathy, systemic vasculitis, sarcoidosis, autoimmune hemolytic anemia, autoimmune thrombocytopenia, thyroiditis, immune-mediated renal disease, a demyelinating disease of the central or peripheral nervous system, idiopathic demyelinating polyneuropathy, Guillain-Barre syndrome, a chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, allergic rhinitis, atopic dermatitis, food hypersensitivity, urticaria, an immunologic disease of the lung, eosinophilic pneumonias, idiopathic pulmonary fibrosis, hypersensitivity pneumonitis, a transplantation associated disease, graft rejection or graft-versus-host-disease, psoriatic arthritis, psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism, autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Sheehan's syndrome, autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis *nodosa*), ankylosing spondylitis, Berger's disease (IgA nephropathy), rapidly progressive glomerulonephritis, primary biliary cirrhosis, Celiac sprue (gluten enteropathy), cryoglobulinemia, and amyotrophic lateral sclerosis (ALS).

The methods of this invention can also be applied to the autoimmune or immune-related diseases or conditions disclosed in, for example, United States Patent Application Publications 20070141625, 20090226440, 20090263474, 20100075891, 20100104579, 20100105086, 20100131286, 20100144055, 20100151471, 20090176217, 20090202469, 20020119118, 20080213280, 20090023166, 20080221016, 20080194474, 20070224638, 20070135335, 20070128189, 20070122413, 20090130683, 20090110667, and 20090023166, and International Patent Application Publications WO/2009/043848, WO/2009/053537, WO/2007/047907, WO/2006/114661, and WO/2003/006058.

As used herein, "treating" a disease or condition refers to taking steps to obtain beneficial or desired clinical results, including clinical results. Beneficial or desired clinical results include, but are not limited to, alleviation or amelioration of one or more symptoms associated with autoimmune or immune-related diseases or conditions.

As used herein, "administering" or "administration of" a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorbtion, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

In certain embodiments, markers used in the methods of invention are up-regulated or activated in the phagocytic cells compared to the non-phagocytic cells. In certain embodiments, markers used in the methods of invention are down-regulated or inhibited in the phagocytic cells compared to the non-phagocytic cells. In certain embodiments, markers used in the methods of invention are up-regulated or activated in the >2n phagocytic cells compared to the =2n phagocytic cells. In certain embodiments, markers used in the methods of invention are down-regulated or inhibited in the >2n phagocytic cells compared to the =2n phagocytic cells. Different diseases or conditions can be associated with either up-regulation (or activation) or down-regulation (or inhibition) of different markers. As used herein, "up-regulation or up-regulated" can refer to an increase in expression levels (e.g., gene expression or protein expression), gene copy numbers, gene dosages, and other qualitative or quantitative detectable state of the markers. Similarly, "down-regulation or down-regulated" can refer to an increase in expression levels, gene copy numbers, gene dosages, and other qualitative or quantitative detectable state of the markers. As used herein, "activation or activated" can refer to an active state of the marker, e.g., a phosphorylation state, a DNA methylation state, or a DNA acetylation state. Similarly, "inhibition or inhibited" can refer to a repressed state or an inactivated state of the marker, e.g., a de-phosphorylation state, a ubiquitination state, a DNA de-methylation state.

In certain embodiments, methods of this invention also comprise at least one of the following steps before determination of various profiles: i) lysing the phagocytic cells and the non-phagocytic cells; ii) extracting cellular contents from the lysed phagocytic cells, the lysed non-phagocytic cells. Any known cell lysis and extraction methods can be used herein. In certain embodiments, the cellular contents of the phagocytic cells comprise various types of materials that they have engulfed, such as, viable diseased cells, dead diseased cells, apoptotic diseased cells, circulating tumor cells, infectious agents, fetal cells, trophoblasts, or fragments thereof. In certain embodiments, at least one or more markers of an autoimmune or immune-related disease or condition are present in the cellular contents of the phagocytic cells. In certain embodiments, there is no marker present in the cellular contents of the non-phagocytic cells.

In certain embodiments, methods of this invention also comprise at least one of the following steps before determination of various profiles: i) lysing the >2n phagocytic cells and the =2n phagocytic cells; and ii) extracting cellular contents from the lysed >2n phagocytic cells and the lysed=2n phagocytic cells. In certain embodiments, the cellular contents of the >2n phagocytic cells comprise various types of materials that they have engulfed, such as, viable diseased cells, dead diseased cells, apoptotic diseased cells, circulating tumor cells, infectious agents, fetal cells, trophoblasts, or fragments thereof. In certain embodiments, at least one or more markers of an autoimmune or immune-related disease or condition are present in the cellular contents of the >2n phagocytic cells. In certain embodiments, there is no marker present in the cellular contents of the =2n phagocytic cells.

In certain embodiments, methods of this invention further comprise comparing the identified difference of the disease or condition-specific markers to a repository of at least one markers known in the art. Such comparison can further confirm the presence of the disease or condition. In some embodiments, the repository of the known markers can be obtained by data mining. The term "data mining", as used herein, refers to a process of finding new data patterns, relations, or correlations derived from the known data of the databases and of extracting practicable information in the future. Typically a computer-based system can be trained on data to perform the data mining, e.g., to classify the input data and then subsequently used with new input data to make decisions based on the training data. These systems include, but are not limited, expert systems, fuzzy logic, non-linear regression analysis, multivariate analysis, decision tree classifiers, and Bayesian belief networks.

In certain embodiments, the phagocytic cells (e.g., the >2n and the =2n subpopulations) and the non-phagocytic cells are isolated from a bodily fluid sample, tissues, or cells. Exemplar bodily fluid sample can be whole blood, urine, stool, saliva, lymph fluid, cerebrospinal fluid, synovial fluid, cystic fluid, ascites, pleural effusion, fluid obtained from a pregnant woman in the first trimester, fluid obtained from a pregnant woman in the second trimester, fluid obtained from a pregnant woman in the third trimester, maternal blood, amniotic fluid, chorionic villus sample, fluid from a preimplantation embryo, maternal urine, maternal saliva, placental sample, fetal blood, lavage and cervical vaginal fluid, interstitial fluid, or ocular fluid. In some embodiments, the phagocytic cells (e.g., the >2n and the =2n subpopulations) and the non-phagocytic cells are isolated from white blood cells. In certain embodiments, the >2n phagocytic cells and the =2n phagocytic cells are separated from a population of phagocytic cells.

In the methods of this invention, cell separation/isolation/purification methods are used to isolate populations of cells from bodily fluid sample, cells, or tissues of a subject. A skilled worker can use any known cell separation/isolation/purification techniques to isolate phagocytic cells or non-phagocytic cells from a bodily fluid, or to separate phagocytic cells from non-phagocytic cells, or to separate >2n phagocytic cells from =2n phagocytic cells. Exemplar techniques include, but are not limited to, using antibodies, flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platform, or a combination thereof.

In certain embodiments, the phagocytic cells and the non-phagocytic cells are isolated by using a product secreted by the phagocytic cells. In certain embodiments, the phagocytic cells and the non-phagocytic cells are isolated by using a cell surface target (e.g., receptor protein) on the surface of phagocytic cells. In some embodiments, the cell surface target is a protein that has been engulfed by the phagocytic cells. In some embodiments, the cell surface target is expressed by the phagocytic cells on their plasma membranes. In some embodiments, the cell surface target is an exogenous protein that is translocated on the plasma membranes, but not expressed by the phagocytic cells. In some embodiments, the cell surface target is a marker of the disease or condition to be detected.

In certain embodiments, the >2n phagocytic cells and the =2n phagocytic cells are isolated by using a product secreted by the >2n phagocytic cells. In certain embodiments, the >2n phagocytic cells and the =2n phagocytic cells are isolated by using a cell surface target (e.g., receptor protein) on the surface of phagocytic cells. In some embodiments, the cell surface target is a protein that has been engulfed by the >2n phagocytic cells. In some embodiments, the cell surface target is expressed by the >2n phagocytic cells on their plasma membranes. In some embodiments, the cell surface target is an exogenous protein that is translocated on the plasma membranes, but not expressed by the >2n phagocytic cells. In some embodiments, the cell surface target is a marker of the disease or condition to be detected.

In certain aspects of the methods described herein, analytes include nucleic acids, proteins, lipids, carbohydrates, metabolites, or any combinations of these. In certain aspects of the methods described herein, markers include nucleic acids, proteins, lipids, carbohydrates, metabolites, or any combinations of these. As used herein, the term "nucleic acid" is intended to include DNA molecules (e.g., cDNA or genomic DNA), RNA molecules (e.g., mRNA), DNA-RNA hybrids, and analogs of the DNA or RNA generated using nucleotide analogs. The nucleic acid molecule can be a nucleotide, oligonucleotide, double-stranded DNA, single-stranded DNA, multi-stranded DNA, complementary DNA, genomic DNA, non-coding DNA, messenger RNA (mR-NAs), microRNA (miRNAs), small nucleolar RNA (snoR-NAs), ribosomal RNA (rRNA), transfer RNA (tRNA), small interfering RNA (siRNA), heterogeneous nuclear RNAs (hnRNA), or small hairpin RNA (shRNA).

As used herein, the term "amino acid" includes organic compounds containing both a basic amino group and an acidic carboxyl group. Included within this term are natural amino acids (e.g., L-amino acids), modified and unusual amino acids (e.g., D-amino acids and β-amino acids), as well as amino acids which are known to occur biologically in free or combined form but usually do not occur in proteins. Natural protein occurring amino acids include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include arginosuccinic acid, citrulline, cysteine sulfuric acid, 3,4-dihydroxyphenylalanine, homocysteine, homoserine, ornithine, 3-monoiodotyrosine, 3,5-diiodotryosine, 3,5,5-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methyl-aminobutyric acid, naphthylalanine, phenylglycine, .alpha.-phenylproline, tert-leucine, 4-aminocyclohexylalanine, N-methyl-norleucine, 3,4-dehydroproline, N,N-dimethyl-aminoglycine, N-methylaminoglycine, 4-aminopiperidine-4-carboxylic acid, 6-aminocaproic acid, trans-4-(aminom-ethyl)-cyclohexanecarboxylic acid, 2-, 3-, and 4-(aminomethyl)-benzoic acid, 1-aminocyclopentanecar-boxylic acid, 1-aminocyclopropanecarboxylic acid, and 2-benzyl-5-aminopentanoic acid.

As used herein, the term "peptide" includes compounds that consist of two or more amino acids that are linked by means of a peptide bond. Peptides may have a molecular weight of less than 10,000 Daltons, less than 5,000 Daltons, or less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog."

As used herein, the term "protein" includes compounds that consist of amino acids arranged in a linear chain and joined together by peptide bonds between the carboxyl and amino groups of adjacent amino acid residues. Proteins used in methods of the invention include, but are not limited to, amino acids, peptides, antibodies, antibody fragments, cytokines, lipoproteins, or glycoproteins.

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or F(ab')$_2$, and Fv). For the structure and properties of the different classes of antibodies, see e.g., Basic and Clinical Immunology, 8th Edition, Daniel P. Sties, Abba I. Ten and Tristram G. Parsolw (eds), Appleton & Lange, Norwalk, Conn., 1994, page 71 and Chapter 6.

As used herein, the term "cytokine" refers to a secreted protein or active fragment or mutant thereof that modulates the activity of cells of the immune system. Examples of cytokines include, without limitation, interleukins, interferons, chemokines, tumor necrosis factors, colony-stimulating factors for immune cell precursors, and the like.

As used herein, the term "lipoprotein" includes negatively charged compositions that comprise a core of hydrophobic cholesteryl esters and triglyceride surrounded by a surface layer of amphipathic phospholipids with which free cholesterol and apolipoproteins are associated. Lipoproteins may be characterized by their density (e.g. very-low-density lipoprotein (VLDL), low-density lipoprotein (LDL) and high density lipoprotein (HDL)), which is determined by their size, the relative amounts of lipid and protein. Lipoproteins may also be characterized by the presence or absence of particular modifications (e.g. oxidization, acetylation, or glycation).

As used herein, the term "glycoprotein" includes glycosides which have one or more oligo- or polysaccharides covalently attached to a peptide or protein. Exemplary glycoproteins can include, without limitation, immunoglobulins, members of the major histocompatibility complex, collagens, mucins, glycoprotein IIb/IIIa, glycoprotein-41 (gp41) and glycoprotein-120 (gp12), follicle-stimulating hormone, alpha-fetoprotein, erythropoietin, transferrins, alkaline phosphatase, and lectins.

As used herein, the term "lipid" includes synthetic or naturally-occurring compounds which are generally amphipathic and biocompatible. Lipids typically comprise a hydrophilic component and a hydrophobic component. Exemplary lipids include, but are not limited to fatty acids, neutral fats, phosphatides, cholesterol, cholesterol esters, triglycerides, glycolipids, glycerolipids, glycerophospholipids, sphingolipids, sterol lipids, prenol lipids, saccharolipids, polyketides, choline glycerophospholipid, ethanolamine glycerophospholipid, phosphatidylinositol, phosphatidylglycerol, phosphatidylserine, lyso-choline glycerophospholipid, lyso-ethanolamine glycerophospholipid, phosphatidic acid, lyso-phosphatidic acid, sphingomyelin, galactosylceramide, glucosylceramide, sulfatide, free fatty acids, prostaglandins, triacylglycerol, diacylglycerol, monoacylglycerol, acyl-CoA, acylcarnitine, oxysterol, ceramide, cardiolipin, sphingoid base-1-phosphate, shingosine, lyso-sphingomyelin, gangliosides, plasmalogen, sulfatide, ceramide, low density lipoproteins (LDLs), very low density lipoproteins (VLDLs), high density lipoproteins (HDLs), sphingoid base-1-phosphates or derivatives thereof.

As used herein, the term "carbohydrate" includes, but is not limited to, compounds that contain oxygen, hydrogen and carbon atoms, typically $(CH_2O)_n$ wherein n is an integer. Exemplary carbohydrates include, but are not limited to, monosaccharides, disaccharides, polysaccharides, or oligosaccharides.

As used herein, the term "metabolite" includes any molecule used in metabolism. Metabolites can be products, substrates, or intermediates in metabolic processes. Included within this term are primary metabolites, secondary metabolites, organic metabolites, or inorganic metabolites. Metabolites include, without limitation, amino acids, peptides, acylcarnitines, monosaccharides, lipids and phospholipids, prostaglandins, hydroxyeicosatetraenoic acids, hydroxyoctadecadienoic acids, steroids, bile acids, and glycolipids and phospholipids. Exemplary metabolites can be sphingolipids, glycosphingolipids, sphingosine, ceramide, sphingomyelin, sphingosylphosphorylcholin, dihydrosphingosine, phoshatidylcholine, phosphatidylinositol, phosphatidylserine, lysophoshatidylcholine, lysophosphatidylinositol, lysophosphatidylserine, plasmenylphoshatidylcholine, plasmanylphoshatidylcholine, proteinogenic amino acids, Alanine, Aspartic acid, Glutamic acid, Phenylalanine, Glycine, Histidine, Leucine, Isoleucine, Lysine, Methionine, Proline, Arginine, Serine, Threonine, Valine, Tryptophan, Tyrosine, asymmetrical dimethyl arginine, symmetrical dimethyl arginine, Glutamine, Asparagine, Nitrotyrosine, Hydroxyproline, Kynurenine, 3-Hydroxy kynurenine, non-proteinogenic amino acids, Ornithine, Citrulline, acylcarnitines, carnitine, free carnitine, acylcarnitine, hydroxylacylcarnitine, dicarboxylacylcarnitines, reducing monosaccharides, hexose, pentose, deoxyhexose, creatinine, creatine, spermidine spermine, putrescine, dopamine, serotonin, prostaglandins, hydoxyeicosatetraeneoic acid, Hydroxyoctadecadienoic acid, leukatrienes, thromboxanes, bile acids, sterols, cholesterols, vitamins and cofactors, drugs, and drug metabolites.

In some embodiments of the invention, profiles of at least one or more markers of an autoimmune or immune-related disease or condition are compared. This comparison can be quantitative or qualitative. Quantitative measurements can be taken using any of the assays described herein. For example, sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), polymerase chain reaction (PCR) analysis, quantitative PCR, real-time PCR, fluorescence assay, colorimetric assay, chemiluminescent assay, or a combination thereof.

Quantitative comparisons can include statistical analyses such as t-test, ANOVA, Krustal-Wallis, Wilcoxon, Mann-Whitney, and odds ratio. Quantitative differences can include differences in the levels of markers between profiles or differences in the numbers of markers present between profiles, and combinations thereof. Examples of levels of the markers can be, without limitation, gene expression levels, nucleic acid levels, protein levels, lipid levels, and the like. Qualitative differences can include, but are not limited to, activation and inactivation, protein degradation, nucleic acid degradation, and covalent modifications.

In certain embodiments of the invention, the profile is a nucleic acid profile, a protein profile, a lipid profile, a carbohydrate profile, a metabolite profile, or a combination thereof. The profile can be qualitatively or quantitatively determined.

A nucleic acid profile can be, without limitation, a genotypic profile, a single nucleotide polymorphism profile, a gene mutation profile, a gene copy number profile, a DNA methylation profile, a DNA acetylation profile, a chromosome dosage profile, a gene expression profile, or a combination thereof.

The nucleic acid profile can be determined by any methods known in the art to detect genotypes, single nucleotide polymorphisms, gene mutations, gene copy numbers, DNA methylation states, DNA acetylation states, chromosome dosages. Exemplar methods include, but are not limited to, polymerase chain reaction (PCR) analysis, sequencing analysis, electrophoretic analysis, restriction fragment length polymorphism (RFLP) analysis, Northern blot analysis, quantitative PCR, reverse-transcriptase-PCR analysis (RT-PCR), allele-specific oligonucleotide hybridization analysis, comparative genomic hybridization, heteroduplex mobility assay (HMA), single strand conformational polymorphism (SSCP), denaturing gradient gel electrophisis (DGGE), RNAase mismatch analysis, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ion-ization-Fourier transform-ion cyclotron resonance (MALDI-FT-ICR) mass spectrometry, secondary ion mass spectrometry (SIMS), surface plasmon resonance, Southern blot analysis, in situ hybridization, fluorescence in situ hybridization (FISH), chromogenic in situ hybridization (CISH), immunohistochemistry (IHC), microarray, comparative genomic hybridization, karyotyping, multiplex ligation-dependent probe amplification (MLPA), Quantitative Multiplex PCR of Short Fluorescent Fragments (QMPSF), microscopy, methylation specific PCR (MSP) assay, HpaII tiny fragment Enrichment by Ligation-mediated PCR (HELP) assay, radioactive acetate labeling assays, colorimetric DNA acetylation assay, chromatin immunoprecipitation combined with microarray (ChIP-on-chip) assay, restriction landmark genomic scanning, Methylated DNA immunoprecipitation (MeDIP), molecular break light assay for DNA adenine methyltransferase activity, chromatographic separation, methylation-sensitive restriction enzyme analysis, bisulfite-driven conversion of non-methylated cytosine to uracil, methyl-binding PCR analysis, or a combination thereof.

As used herein, the term "sequencing" is used in a broad sense and refers to any technique known in the art that allows the order of at least some consecutive nucleotides in at least part of a nucleic acid to be identified, including without limitation at least part of an extension product or a vector insert. Exemplar sequencing techniques include direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In some embodiments, sequencing comprises an detecting the sequencing product using an instrument, for example but not limited to an ABI PRISM® 377 DNA Sequencer, an ABI PRISM® 310, 3100, 3100-Avant, 3730, or 3730xI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

In further embodiments of the invention, a protein profile can be a protein expression profile, a protein activation profile, or a combination thereof. In some embodiments, a protein activation profile can comprise determining a phosphorylation state, an ubiquitination state, a myristoylation state, or a conformational state of the protein.

A protein profile can be detected by any methods known in the art for detecting protein expression levels, protein phosphorylation state, protein ubiquitination state, protein myristoylation state, or protein conformational state. In some embodiments, a protein profile can be determined by an immunohistochemistry assay, an enzyme-linked immunosorbent assay (ELISA), in situ hybridization, chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microscopy, microfluidic chip-based assays, surface plasmon resonance, sequencing, Western blotting assay, or a combination thereof.

In some embodiments of the invention, a lipid profile can be determined by chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microfluidic chip-based assay, detection of fluorescence, detection of chemiluminescence, or a combination thereof. Further methods for analyzing lipid content in a biological sample are known in the art (See, e.g., Kang et al. (1992) Biochim. Biophys. Acta. 1128:267; Weylandt et al. (1996) Lipids 31:977; J. Schiller et al. (1999) Anal. Biochem. 267:46; Kang et al. (2001) Proc. Natl. Acad. Sci. USA 98:4050; Schiller et al. (2004) Prog. Lipid Res. 43:499). One exemplary method of lipid analysis is to extract lipids from a biological sample (e.g. using chloroform-methanol (2:1, vol/vol) containing 0.005% butylated hydroxytoluene (BHT, as an antioxidant)), prepare fatty acid methyl esters (e.g., using 14% BF3-methanol reagent), and quantify the fatty acid methyl esters (e.g., by HPLC, TLC, by gas chromatography-mass spectroscopy using commercially available gas chromatographs, mass spectrometers, and/or combination gas chromatograph/mass spectrometers). Fatty acid mass is determined by comparing areas of various analyzed fatty acids to that of a fixed concentration of internal standard.

In some embodiments of the invention, a carbohydrate profile can be determined by chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microfluidic chip-based assay, detection of fluorescence, detection of chemiluminescence, or a combination thereof.

In some embodiments of the invention, a metabolite profile can be determined by chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microfluidic chip-based assay, detection of fluorescence, detection of chemiluminescence, or a combination thereof.

As used herein, the "difference" between different profiles detected by the methods of this invention can refer to different gene copy numbers, different DNA, RNA, protein, lipid, or carbohydrate expression levels, different DNA methylation states, different DNA acetylation states, and different protein modification states. The difference can be a difference greater than 1 fold. In some embodiments, the difference is a 1.05-fold, 1.1-fold, 1.2-fold, 1.3-fold, 1.4-fold, 1.5-fold, 2-fold, 2.5-fold, 3-fold, 4-fold, 5-fold, 6-fold, 7-fold, 8-fold, 9-fold, or 10-fold difference. In some embodiments, the difference is any fold difference between 1-10, 2-10, 5-10, 10-20, or 10-100 folds.

A general principle of assays to detect markers involves preparing a sample or reaction mixture that may contain the marker (e.g., one or more of DNA, RNA, protein, polypeptide, carbohydrate, lipid, metabolite, and the like) and a probe under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In certain exemplary embodiments, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, U.S. Pat. Nos. 5,631,169 and 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C, 1991, Anal. Chem. 63:2338 2345 and Szabo et al, 1995, Curr. Opin. Struct. Biol. 5:699 705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas and Minton (1993) Trends Biochem. Sci. 18:284). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard (1998) J. Mol. Recognit. 11:141; Hage and Tweed (1997) J. Chromatogr. B. Biomed. Sci. Appl. 12:499). Gel electrophoresis may also be employed to separate complexed assay components from unbound components (see, e.g., Ausubel et al, ed., Current Protocols in Molecular Biology, John Wiley & Sons, New York, 1987 1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In certain exemplary embodiments, the level of mRNA corresponding to the marker can be determined either by in situ and/or by in vitro formats in a biological sample using methods known in the art. Many expression detection methods use isolated RNA. For in vitro methods, any RNA isolation technique that does not select against the isolation of mRNA can be utilized for the purification of RNA from blood cells (see, e.g., Ausubel et al, ed., Current Protocols in Molecular Biology, John Wiley & Sons, New York 1987 1999). Additionally, large numbers of cells and/or samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. In certain exemplary embodiments, a diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by RT-PCR (the experimental embodiment set forth in U.S. Pat. Nos. 4,683,195 and 4,683,202), COLD-PCR (Li et al. (2008) Nat. Med. 14:579), ligase chain reaction (Barany, 1991, Proc. Natl. Acad. Sci. USA, 88:189), self sustained sequence replication (Guatelli et al., 1990, Proc. Natl. Acad. Sci. USA 87:1874), transcriptional amplification system (Kwoh et al. (1989) Proc. Natl. Acad. Sci. USA 86:1173), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the sample (e.g., a bodily fluid (e.g., blood cells)) prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in a patient sample from one source to a patient sample from another source, e.g., to compare a phagocytic blood cell from an individual to a non-phagocytic blood cell from the individual.

In one embodiment of this invention, a protein or polypeptide corresponding to a marker is detected. In certain embodiments, an agent for detecting a protein or polypeptide can be an antibody capable of binding to the polypeptide, such as an antibody with a detectable label. As used herein, the term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. Antibodies can be polyclonal or monoclonal. An intact antibody, or a fragment thereof (e.g., Fab or F(ab')2) can be used. In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well known supports or carriers include glass, polystyrene, polypropylene, polyethylene, dextran, nylon, amylases, natural and modified celluloses, polyacrylamides, gabbros, magnetite and the like.

A variety of formats can be employed to determine whether a sample contains a protein that binds to a given antibody. Examples of such formats include, but are not limited to, competitive and non-competitive immunoassay, enzyme immunoassay (EIA), radioimmunoassay (RIA), antigen capture assays, two-antibody sandwich assays, Western blot analysis, enzyme linked immunoabsorbant assay (ELISA), a planar array, a colorimetric assay, a chemiluminescent assay, a fluorescent assay, and the like. Immunoassays, including radioimmunoassays and enzyme-linked immunoassays, are useful in the methods of the present invention. A skilled artisan can readily adapt known protein/antibody detection methods for use in determining whether cells (e.g., bodily fluid cells such as blood cells) express a marker of the present invention. One skilled in the art will know many other suitable carriers for binding antibody or antigen, and will be able to adapt such support for use with the present invention. For example, protein isolated from cells (e.g., bodily fluid cells such as blood cells) can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In certain exemplary embodiments, assays are provided for diagnosis, prognosis, assessing the risk of developing a disease, assessing the efficacy of a treatment, monitoring the progression or regression of a disease, and identifying a compound capable of ameliorating or treating a disease. An exemplary method for these methods involves obtaining a bodily fluid sample from a test subject and contacting the bodily fluid sample with a compound or an agent capable of detecting one or more of the markers of the disease or condition, e.g., marker nucleic acid (e.g., mRNA, genomic DNA), marker peptide (e.g., polypeptide or protein), marker lipid (e.g., cholesterol), or marker metabolite (e.g., creatinine) such that the presence of the marker is detected in the biological sample. In one embodiment, an agent for detecting marker mRNA or genomic DNA is a labeled nucleic acid probe capable of hybridizing to marker mRNA or genomic DNA. The nucleic acid probe can be, for example, a full-length marker nucleic acid or a portion thereof. Other suitable probes for use in the diagnostic assays of the invention are described herein.

As used herein, a compound capable of ameliorating or treating an autoimmune or immune-related disease or condition can include, without limitations, any substance that can improve symptoms or prognosis, prevent progression of the disease or condition, promote regression of the disease or condition, or eliminate the disease or condition.

In yet another aspect, this invention provides a method for identifying a compound capable of ameliorating or treating an autoimmune or immune-related disease or condition in a subject comprising: a) determining a first profile of one or more markers of the disease or condition from a population of >2n phagocytic cells from the subject before administering the compound to the subject; determining a second profile of at least one of the one or more markers from a population of =2n phagocytic cells from the subject before administering the compound to the subject; identifying a first difference between the first and second profiles of at least one or more of said markers; b) determining a third profile of the one or more markers from a population of >2n phagocytic cells from the subject after the administration of the compound; determining a fourth profile of at least one of the one or more markers from a population of =2n phagocytic cells from the subject after the administration of the compound; identifying a second difference between the third and fourth profiles of at least one or more of said markers; c) identifying a difference between the first difference and the second difference, wherein the identified difference indicates that the compound is capable of ameliorating or treating said disease or condition in the subject.

In yet another aspect, this invention provides a method for identifying one or more markers for an autoimmune or immune-related disease or condition comprising: a) determining a first profile of analytes from phagocytic cells from a subject having said disease or condition; determining a second profile of analytes from non-phagocytic cells from the subject having said disease or condition; identifying a first set of differences between the first and second profiles, wherein the first set of differences is specific to the first profile relative to the second profile; b) determining a third profile of analytes from phagocytic cells from a control subject not having said disease or condition; determining a fourth profile of analytes from non-phagocytic cells from the control subject not having said disease or condition; identifying a second set of differences between the third and fourth profiles, wherein the second set of differences is specific to the third profile relative to the fourth profile; c) identifying one or more analytes specific to the first set of differences relative to the second set of differences, the identified analytes being markers of said disease or condition. Optionally, this method further comprises d) obtaining a fifth profile of analytes from cells or tissues affected by said disease or condition in the subject having said disease or condition; obtaining a sixth profile of analytes from cells or tissues not affected by said disease or condition in the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comprising: a) determining a first profile of analytes from phagocytic cells from a subject having said disease or condition; determining a second profile of analytes from phagocytic cells from a control subject not having said disease or condition; identifying a first set of differences between the first and second profiles, wherein the first set of differences is specific to the first profile relative to the second profile; b) determining a third profile of analytes from non-phagocytic cells from the subject having said disease or condition; determining a fourth profile of analytes from non-phagocytic cells from the control subject not having said disease or condition; identifying a second set of differences between the third and fourth profiles, wherein the second set of differences is specific to the third profile relative to the fourth profile; c) identifying one or more analytes specific to the first set of differences relative to the second set of differences, the identified analytes being markers of said disease or condition. And optionally, the method further comprises d) obtaining a fifth profile of analytes from cells or tissues affected by said disease or condition in the subject having said disease or condition; obtaining a sixth profile of analytes from cells or tissues not affected by said disease or condition in the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comprising: a) determining a first profile of analytes from phagocytic cells from a subject having said disease or condition; obtaining a second profile of analytes from phagocytic cells from a control subject not having said disease or condition by data mining; identifying a first set of differences between the first and second profiles, wherein the first set of differences is specific to the first profile relative to the second profile; b) determining a third profile of analytes from non-phagocytic cells from the subject having said disease or condition; obtaining a fourth profile of analytes from non-phagocytic cells from a control subject not having said disease or condition by data mining; identifying a second set of differences between the third and fourth profiles, wherein the second set of differences is specific to the third profile relative to the fourth profile; and c) identifying one or more analytes specific to the first set of differences relative to the second set of differences, the identified analytes being markers of said disease or condition. And optionally, the method further comprises d) obtaining a fifth profile of analytes from cells or tissues affected by said disease or condition by data mining; obtaining a sixth profile of analytes from cells or tissues not affected by said disease or condition by data mining; identifying a third set of differences between the fifth and sixth profiles, wherein the third set of differences is specific to the fifth profile relative to the sixth profile; and e) identifying at least one of the one or more markers of c) present in the third set of differences.

In yet another aspect, this invention provides a method for identifying one or more markers of an autoimmune or immune-related disease or condition comprising: a) determining a first profile of analytes from phagocytic cells from a subject having said disease or condition; determining a second profile of analytes from non-phagocytic cells from the subject having said disease or condition; identifying a first set of differences between the first and second profiles, wherein the first set of differences is specific to the first profile relative to the second profile; b) determining a third profile of analytes from cells or tissues affected by said disease or condition from the subject having said disease or condition; determining a fourth profile of analytes from cells or tissues not affected by said disease or condition from the subject having said disease or condition; identifying a second set of differences between the third and fourth profiles, wherein the second set of differences is specific to the third profile relative to the fourth profile; c) identifying one or more analytes present in both the first set of differences and the second set of differences, the identified analytes being markers of said disease or condition. And optionally, the method further comprises d) determining a fifth profile of analytes from phagocytic cells from a control subject not having said disease or condition; identifying a third set of differences between the first and fifth profiles, wherein the third set of differences is specific to the first profile relative to the fifth profile; e) identifying at least one of the one or more markers of c) present in the third set of differences.

In yet another aspect, this invention provides a method for identifying one or more markers of an autoimmune or immune-related disease or condition comprising: a) determining a first profile of analytes from >2n phagocytic cells from a subject having said disease or condition; determining a second profile of analytes from =2n phagocytic cells from the subject having said disease or condition; identifying a first set of differences between the first and second profiles, wherein the first set of differences is specific to the first profile relative to the second profile; b) determining a third profile of analytes from >2n phagocytic cells from a control subject not having said disease or condition; determining a fourth profile of analytes from =2n phagocytic cells from the control subject not having said disease or condition; identifying a second set of differences between the third and fourth profiles, wherein the second set of differences is specific to the third profile relative to the fourth profile; and c) identifying one or more analytes specific to the first set of differences relative to the second set of differences, the identified analytes being markers of said disease or condition. And optionally, the method further comprises: d) obtaining a fifth profile of analytes from cells or tissues affected by said disease or condition from the subject having said disease or condition; obtaining a sixth profile of analytes from cells or tissues not affected by said disease or condition from the subject having said disease or condition; identifying a third set of differences between the fifth and sixth profiles, wherein the third set of differences is specific to the fifth profile relative to the sixth profile; and e) identifying at least one of the one or more markers of c) present in the third set of differences.

An exemplary method for detecting the presence or absence of an analyte (e.g., DNA, RNA, protein, polypeptide, carbohydrate, lipid or the like) corresponding to a marker of the invention in a biological sample involves obtaining a bodily fluid sample (e.g., blood) from a test subject and contacting the bodily fluid sample with a compound or an agent capable of detecting one or more markers. Detection methods described herein can be used to detect one or more markers in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques. Because each marker is also an analyte, any method described herein to detect the presence or absence of a marker can also be used to detect the presence or absence of an analyte.

The marker that is useful in the methods of the invention includes those disclosed in, for example, U.S. Pat. Nos. 7,604,948, 7,670,764, 6,986,995, and 6,631,415, United States Patent Application Publication 20070141625, 20090263474, 20100075891, 20100104579, 20100105086, 20100131286, 20090176217, 20090202469, 20020119118, 20090258025, 20100137393, 20100120629, 20090318392, 20090196927, 20090023166, 20080227709, 20080039402, 20080026378, 20070224638, 20070218519, 20060210562, 20050266432, 20050164233, 20050130245, 20090130683, 20090110667, 20090054321, 20090023166, and 20080274118, and International Patent Application Publication WO/2009/043848, WO/2010/053587, WO/2010/046503, WO/2010/039714, WO/2009/100342, WO/2009/053537, WO/2009/017444, WO/2008/156867, WO/2008/147938, WO/2008/129296, WO/2008/137835, WO/2008/082519, WO/2008/064336, WO/2008/043782, WO/2008/043725, WO/2007/047907, WO/2006/125117, WO/2006/114661, WO/2006/020899, WO/2005/114222, WO/2005/007836, WO/2004/076639, WO/2004/050704, and WO/2001/014881.

The marker that is useful in the methods of the invention can also include those markers disclosed in, for example, R M O'Hara, Jr, et al., *Drug Discovery Today* (2006), 11:342-347; HE Prince, *Biomarkers* (2005), 10 Suppl 1:S44-S49; C Selmi and ME Gershwin, *Gut* (2010), 59:712-713; K Ray, *Nature Reviews Rheumatology* (2010) 6:380; GP Blaney et al., *Ann N Y Acad Sci* (2009), 1173:384-390; W Hueber and WH Robinson, *Proteomics* (2006), 6:4100-4105.

The marker that is useful in the methods of the invention can include any mutation in any one of the above-identified markers. Mutation sites and sequences can be identified, for example, by databases or repositories of such information, e.g., The Human Gene Mutation Database (www.hgmd.cf.ac.uk), the Single Nucleotide Polymorphism Database (dbSNP, www.ncbi.nlm.nih.gov/projects/SNP), and the Online Mendelian Inheritance in Man (OMIM) website (www.ncbi.nlm.nih.gov/omim).

The marker that is useful in the methods of the invention can include any marker that is known to be associated with an autoimmune or immune-related disease or condition.

The present invention also provides kits that comprise marker detection agents that detect at least one or more of the markers identified by the methods of this invention. This present invention also provides methods of treating or preventing an autoimmune or immune-related disease or condition in a subject comprising administering to said subject an agent that modulates the activity or expression of at least one or more of the markers identified by the methods of this invention.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

The following examples are set forth as being representative of the present invention. These examples are not to be construed as limiting the scope of the invention as these and other equivalent embodiments will be apparent in view of the present disclosure, figures, and accompanying claims.

EXAMPLES

Example 1

Figure 1C:
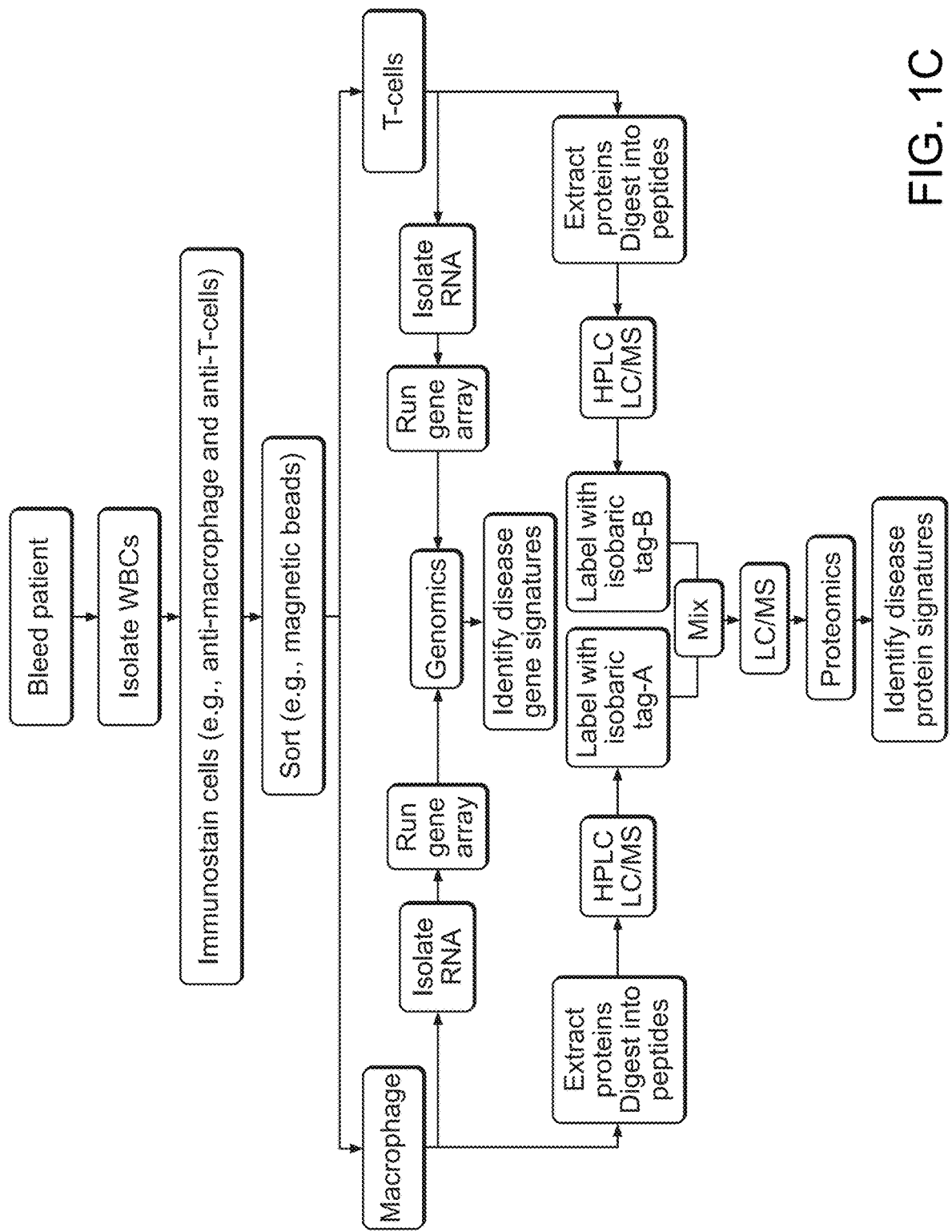
FIG. 1C schematically depicts a general flowchart of one embodiment of a method of the invention.

A Representative Method for the Separation of Phagocytic Cells from Non-Phagocytic Cells and the Analysis of Expression Profiles 1. With reference to FIG. 1C, coat plates with avidin.
2. Add biotinylated antibody to non-phagocytic blood cell (e.g., T cells) to the wells, incubate for 30 min at RT, wash wells.
3. Add magnetic beads.
4. Add WBC blood sample.
5. Incubate at 37° C. (30 minutes-1 hour).
6. Following phagocytosis of beads by phagocytic cells and binding of avidin-biotin-antibody to non-phagocytic cells, place plate on top of magnet and wash (the phagocytic cells that internalized the magnetic beads and the non-phagocytic cells bound to the antibody will stay; all other cells will be washed away).
7. Remove magnet and collect phagocytic cells.
8. Isolate RNA from phagocytic cells (e.g., cells bound to a magnetic bead) and of non-phagocytic cells (e.g., those cells attached to the bottom of the wells via the anti-non-phagocytic cell biotinylated antibody-avidin bound), prepare cDNA, cRNA and use to differentiate genetic profiles (e.g., whole gene arrays and/or cancer gene arrays) of phagocytic and non-phagocytic cells.
9. Isolate DNA from each cell sample and identify disease-DNA signatures selectively present in phagocytes (i.e., absent in non-phagocytes); compare the profiles (e.g., whole gene arrays, DNA mutations and/or SNPs obtained in phagocytic and non-phagocytic cells).
10. Isolate protein from each cell sample, run Western blots using antibodies to known proteins overexpressed in an individual with an autoimmune or immune-related disease or condition, and compare the profiles obtained in phagocytic and non-phagocytic cells. Alternatively, use mass spectroscopy to identify the proteins.
11. Isolate lipids from each cell sample and compare quantity and quality, for example using HPLC.

Example 2

A Representative Method for the Separation of Phagocytic Cells from Non-Phagocytic Cells and the Analysis of Expression Profiles 1. With reference to FIG. 1C, lyse RBCs in blood sample.
2. Cytospin WBC on glass slides.

3. Fix cells in acetone/methanol (−20° C. for 5 minutes).

4. Stain with hematoxylin and eosin stain and anti-T cell antibody.

5. Isolate T cells (non-phagocytic) and macrophages (phagocytic) using laser capture microscopy (LCM).

6. Isolate RNA from phagocytic cells and of non-phagocytic cells, prepare cDNA, cRNA and use to differentiate genetic profiles (e.g., whole gene arrays and/or disease gene arrays) of phagocytic and non-phagocytic cells.

7. Isolate DNA from each cell sample, run DNA arrays, and compare the profiles (e.g., whole gene arrays, DNA mutations and/or SNPs) obtained in phagocytic and non-phagocytic cells.

8. Isolate protein from each cell sample, run Western blots using antibodies to known proteins overexpressed in an individual with an autoimmune or immune-related disease or condition, and compare the profiles obtained in phagocytic and non-phagocytic cells. Alternatively, use mass spectroscopy to identify the proteins.

9. Isolate lipids from each cell sample and compare quantity and quality, for example using HPLC.

Example 3

A Representative Method for the Separation of Phagocytic Cells from Non-Phagocytic Cells and the Analysis of Expression Profiles 1. With reference to FIG. 1C, lyse RBC from a blood sample.

2. Use magnetic antibody-conjugated beads to isolate non-phagocytic (e.g., T cells) and phagocytic cells (e.g., neutrophils and/or macrophages and/or monocytes) from whole blood.

3. Isolate RNA from each cell sample, prepare cDNA, cRNA and use to differentiate genetic profiles (e.g., cancer gene array) of phagocytic and non-phagocytic cells.

4. Isolate DNA from each cell sample, run DNA arrays, and compare the profiles obtained in phagocytic and non-phagocytic cells.

5. Isolate protein from each cell sample, run Western blots using antibodies to known proteins overexpressed in an individual with an autoimmune or immune-related disease or condition, and compare the profiles obtained in phagocytic and non-phagocytic cells. Alternatively, use mass spectroscopy to identify the proteins.

6. Isolate lipids from each cell sample and compare quantity and quality, for example using HPLC.

Example 4

A Representative Method for the Separation of Phagocytic Cells from Non-Phagocytic Cells and the Analysis of Expression Profiles 1. With reference to FIG. 1C, stain WBC with fluorescent antibodies specific against a particular cell subpopulation (e.g., neutrophils, macrophages, monocytes, T cells and the like).

2. Sort the cells (e.g., by FACS).

3. Isolate RNA from each cell sample, prepare cDNA, cRNA and use to differentiate genetic profiles (e.g., gene array) of phagocytic and non-phagocytic cells.

4. Isolate DNA from each cell sample, run DNA arrays, and compare the profiles obtained in phagocytic and non-phagocytic cells.

5. Isolate protein from each cell sample, run Western blots using antibodies to known proteins overexpressed in an individual with an autoimmune or immune-related disease or condition, and compare the profiles obtained in phagocytic and non-phagocytic cells. Alternatively, use mass spectroscopy to identify the proteins.

6. Isolate lipids from each cell sample and compare quantity and quality, for example using HPLC.

Example 5

Figure 1D:
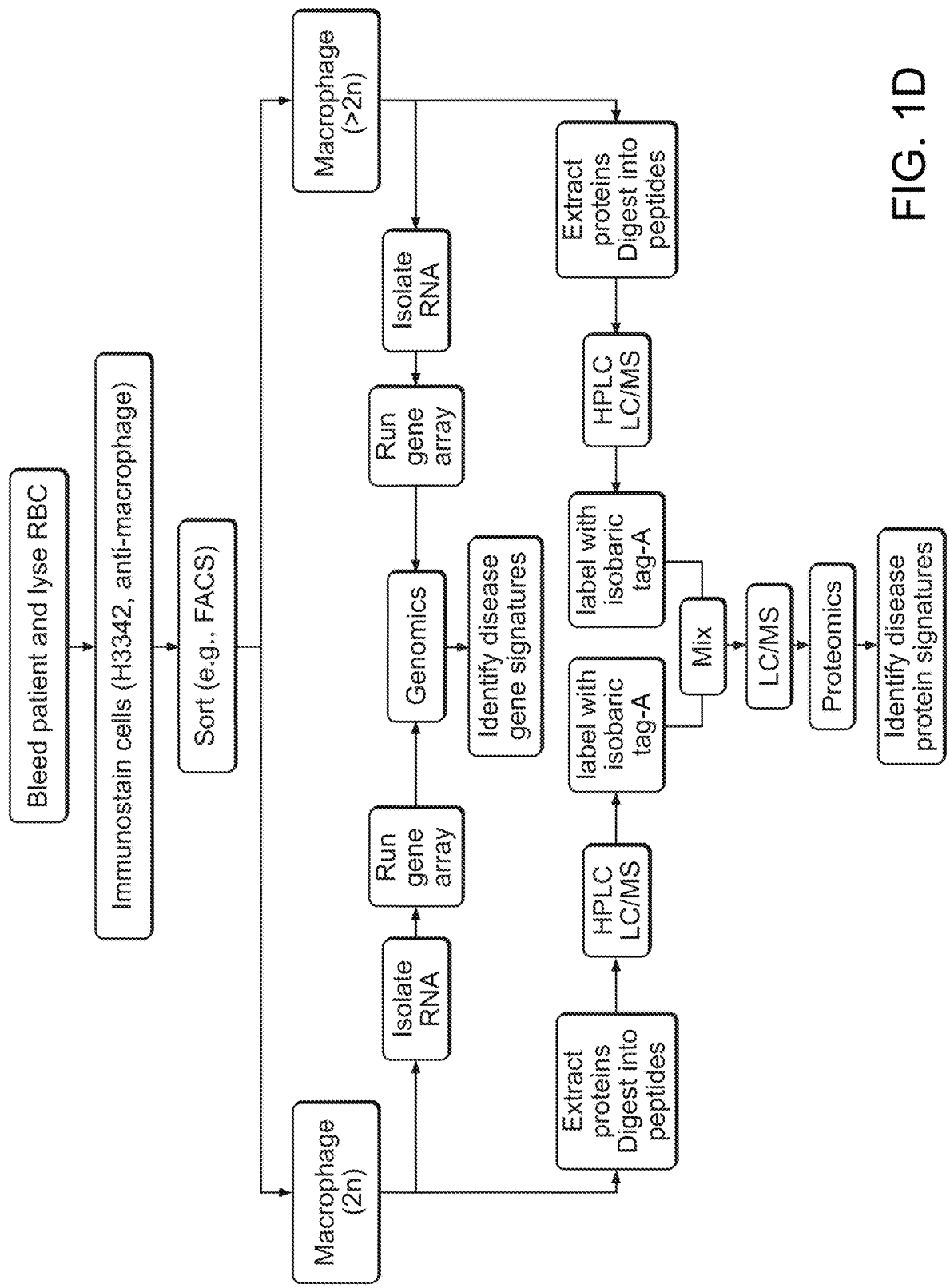
FIG. 1D schematically depicts a general flowchart of one embodiment of a method of the invention.
Figure 2A:
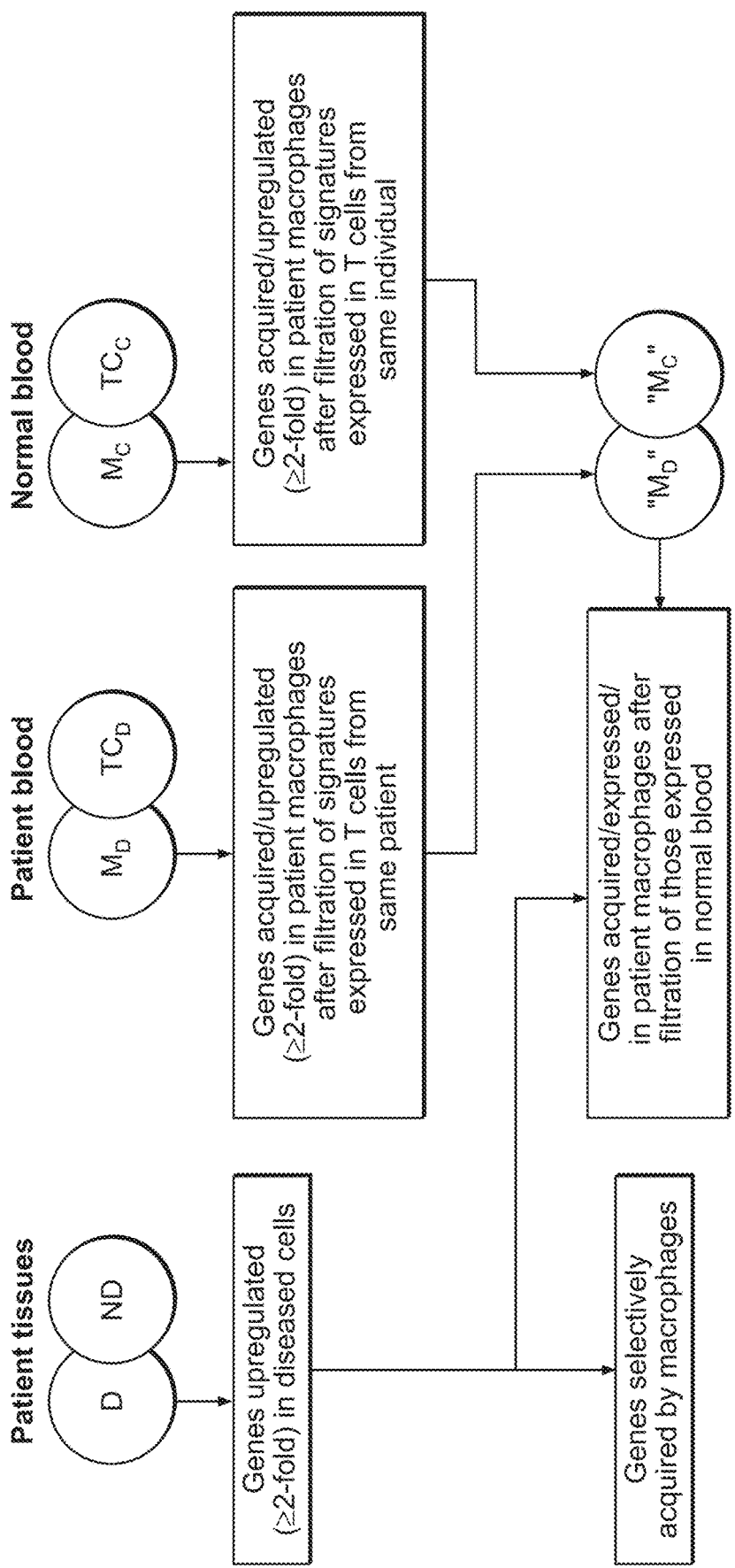
FIG. 2A schematically depicts one embodiment of a method of this invention for identifying one or more markers of an autoimmune or immune-related disease or condition. D represents diseased cells/tissues from a patient having an autoimmune or immune-related disease or condition; and ND represents not-diseased cells/tissues from the patient; $M_D$ represents macrophages taken from the patient; $TC_D$ represents T cells taken from the patient(s); $M_C$ represents macrophages taken from a control subject not having the disease or condition; $TC_C$ represents T cells taken from the control subject.
Figure 2B:
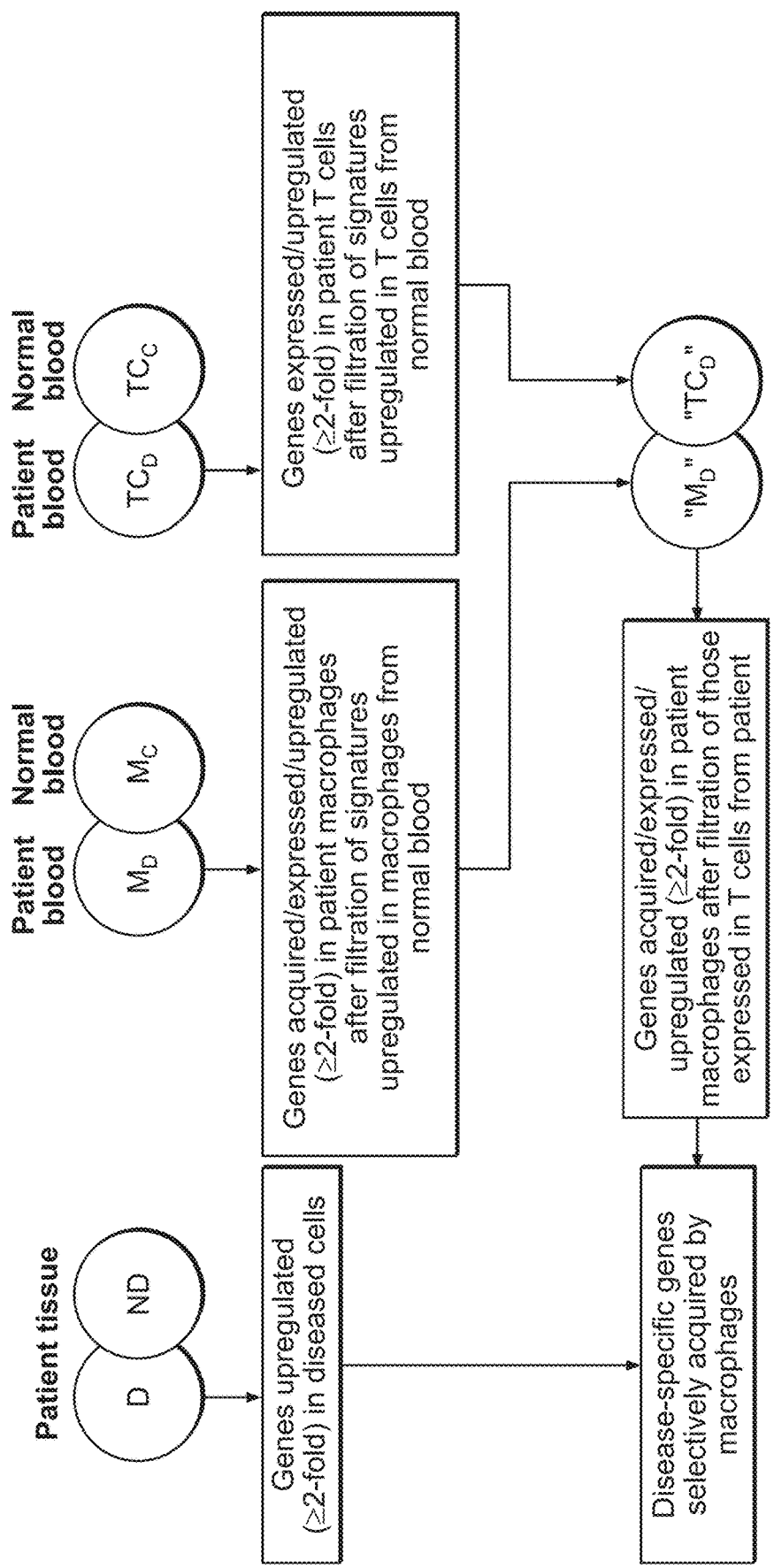
FIG. 2B schematically depicts one embodiment of a method of this invention for identifying one or more markers of an autoimmune or immune-related disease or condition. D represents diseased cells/tissues from a patient having an autoimmune or immune-related disease or condition; and ND represents not-diseased cells/tissues from the patient; $M_D$ represents macrophages taken from the patient; $TC_D$ represents T cells taken from the patient; $M_C$ represents macrophages taken from a control subject not having the disease or condition; $TC_C$ represents T cells taken from the control subject.
Figure 2C:
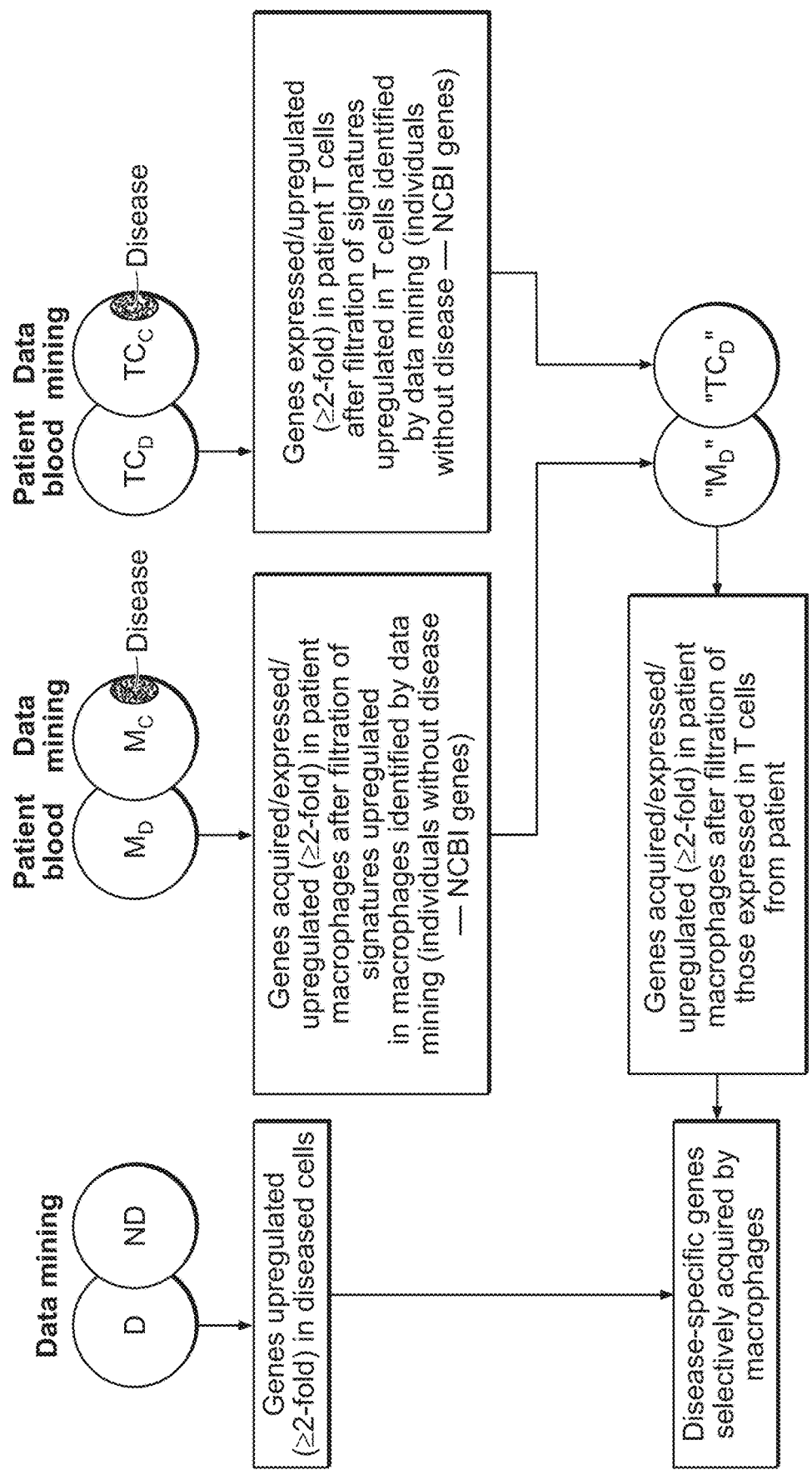
FIG. 2C schematically depicts one embodiment of a method of this invention for identifying one or more markers of an autoimmune or immune-related disease or condition. D represents information obtained by data mining about diseased cells/tissues from patients having an autoimmune or immune-related disease or condition; and ND represents information obtained by data mining about not-diseased cells/tissues from patients having the same disease or condition; $M_D$ represents macrophages taken from a patient having the disease or condition; $TC_D$ represents T cells taken from the patient; $M_C$ represents information obtained by data mining about macrophages from control subjects not having the disease or condition; $TC_C$ represents information obtained by data mining about T cells obtained from control subjects not having the disease or condition.
Figure 3:
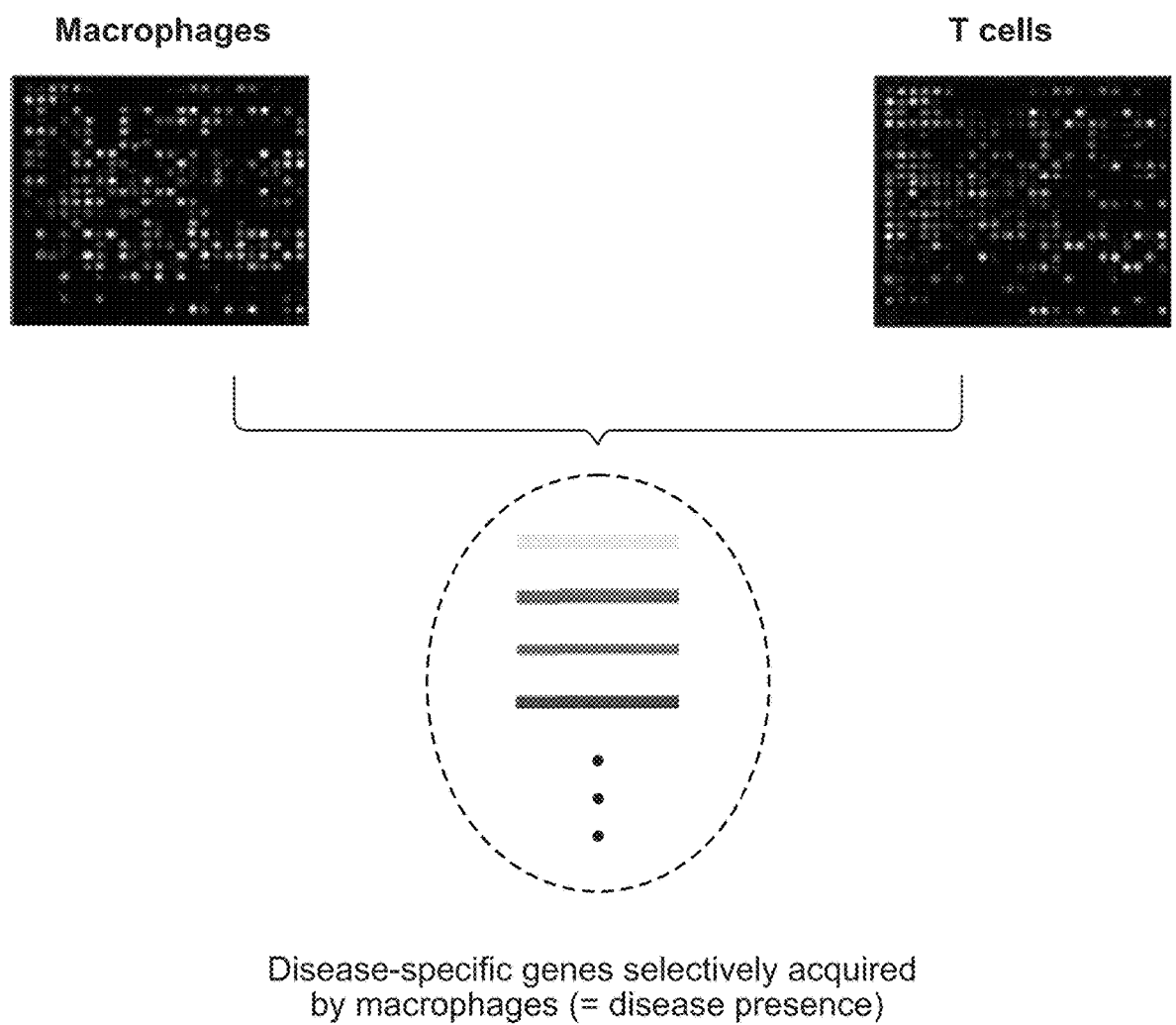
FIG. 3 depicts a schematic of gene expression profile data that could be compared to identify autoimmune or immune-related disease-specific genes selectively acquired/expressed by macrophages.
Figure 4A:
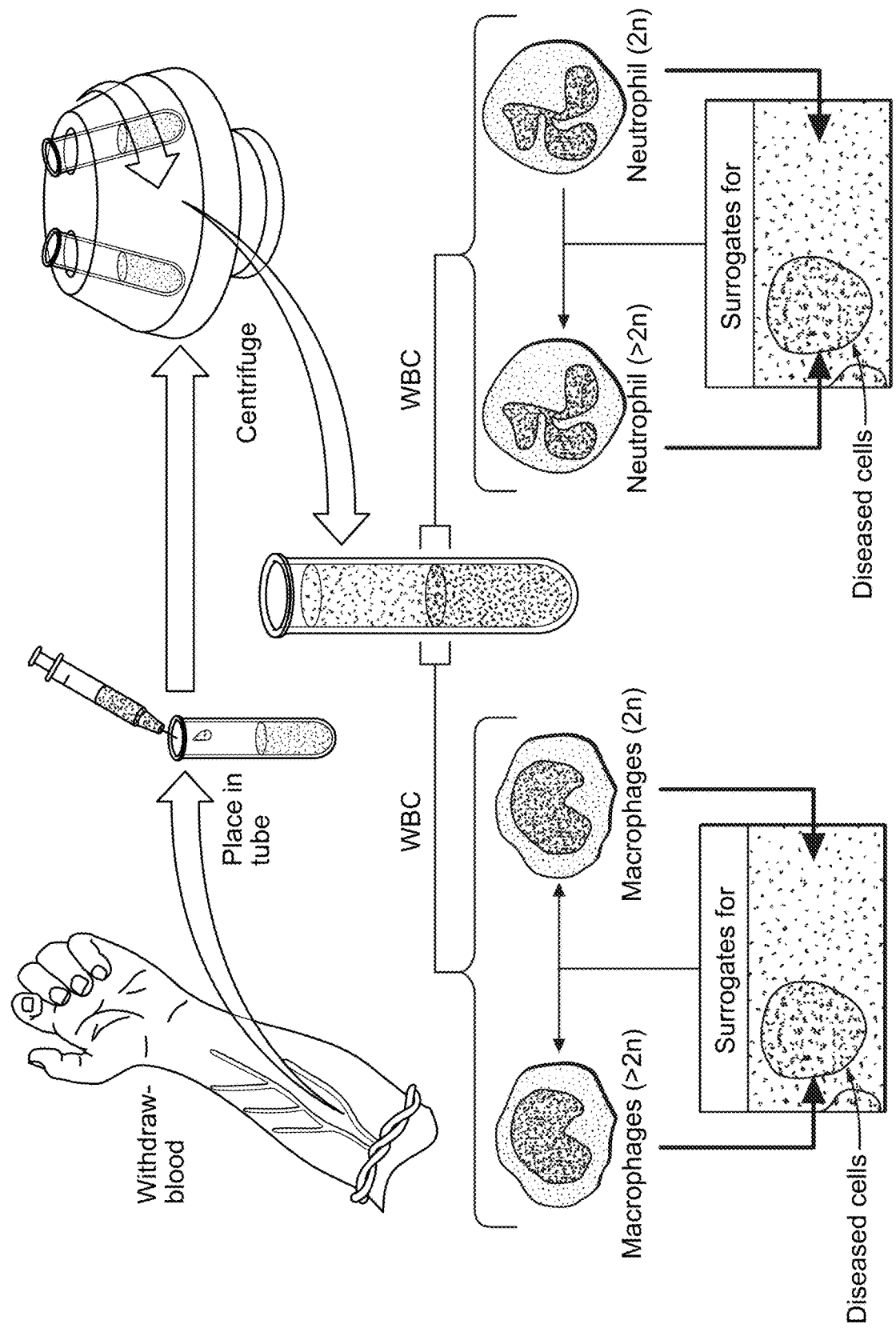
FIG. 4A schematically depicts one embodiment of a method of this invention for diagnosing or aiding in the diagnosis of an autoimmune or immune-related disease or condition. In this embodiment, a blood sample is withdrawn from an individual to be diagnosed. After a centrifugation step, white blood cells are isolated from the blood sample and further separated into two populations of phagocytic cells: phagocytic cells (e.g., macrophages or neutrophils) having a DNA content more than 2n (>2n phagocytic cells) and phagocytic cells (e.g., macrophages or neutrophils) having a DNA content of 2n (=2n phagocytic cells). The >2n phagocytic cells serve as surrogates for diseased cells and the 2n phagocytic cells serve as control cells.
Figure 4B:
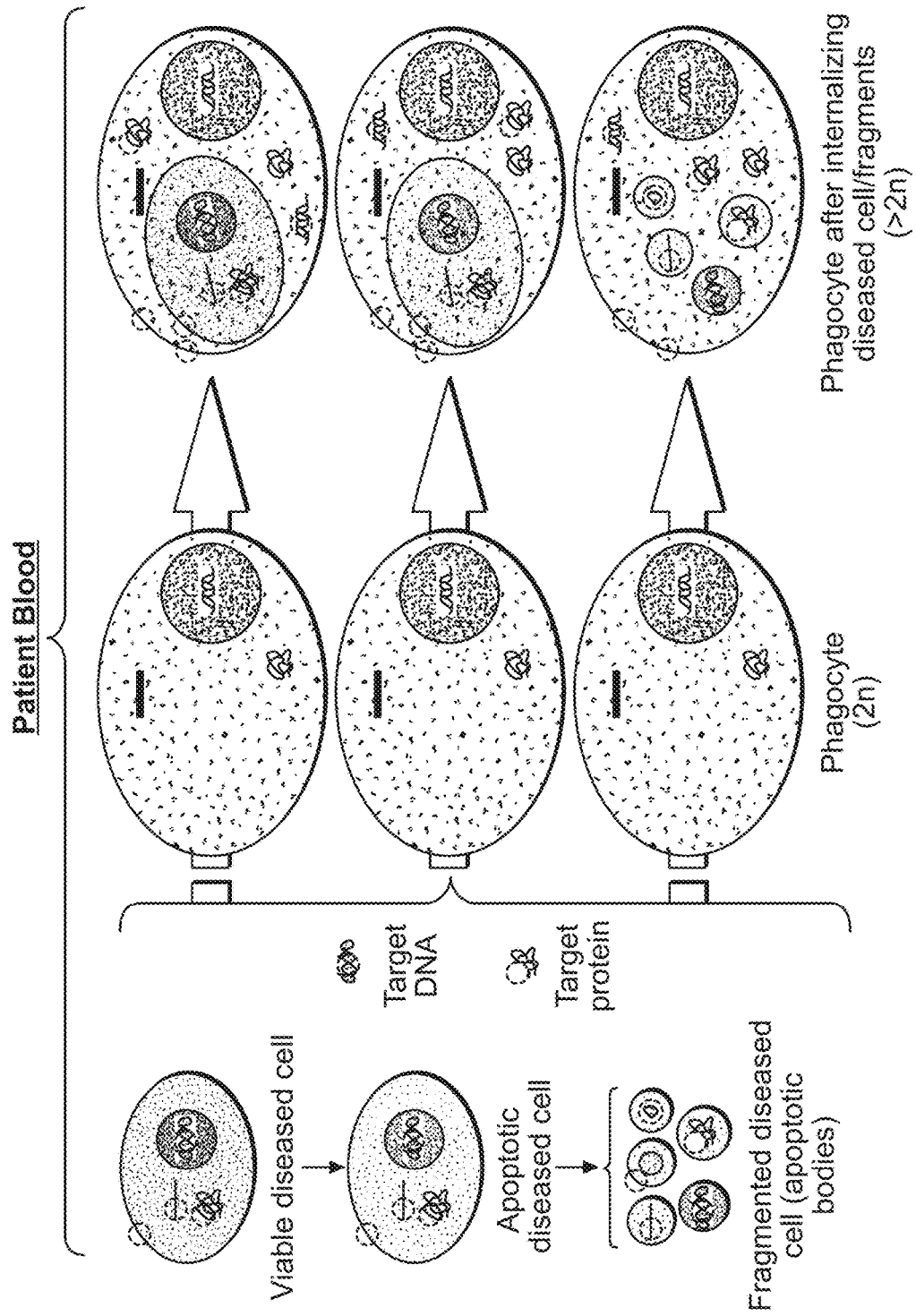
FIG. 4B schematically depicts one proposed pathway leading to acquisition of autoimmune or immune-related disease or condition-specific markers (e.g., DNA, RNA, protein and lipid markers) by phagocytic cells. Blood phagocytes engulf viable circulating diseased cells, apoptotic diseased cells, and/or fragmented diseased cells. Accordingly, the autoimmune or immune-related disease or condition-specific markers (e.g., DNAs, RNAs, proteins, or lipids) that are contained within these diseased cells/fragments are also internalized by phagocytic cells, which then become >2n phagocytic cells containing and/or expressing these specific markers. By contrast, phagocytic cells that do not internalize these diseased cells/fragments, and thus, do not contain or express these markers, and remain DNA content of 2n.
Figure 5:
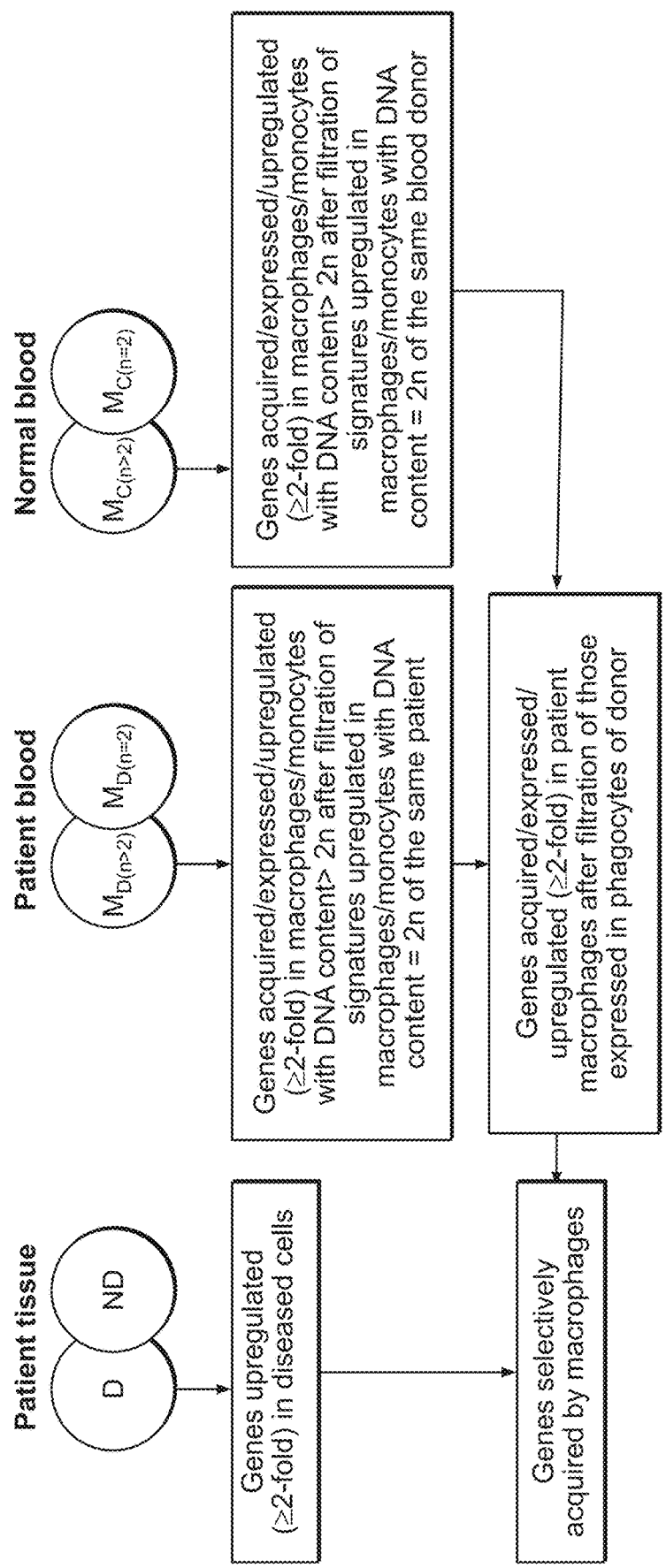
FIG. 5 schematically depicts one embodiment of a method of this invention for identifying one or more markers of an autoimmune or immune-related disease or condition. D represents diseased tissues/cells from a patient having an autoimmune or immune-related disease or condition; and ND represents not-diseased tissues/cells from the patient; $M_{D(N>2)}$ represents macrophages having a DNA content of >2n taken from a patient with the disease or condition; $M_{D(N=2)}$ represents macrophages having a DNA content of =2n taken from the patient; $M_{C(N>2)}$ represents macrophages having a DNA content of >2n taken from a control subject not having the disease or condition; $M_{C(N=2)}$ represents macrophages having a DNA content of >2n taken from the control subject.
Figure 6:
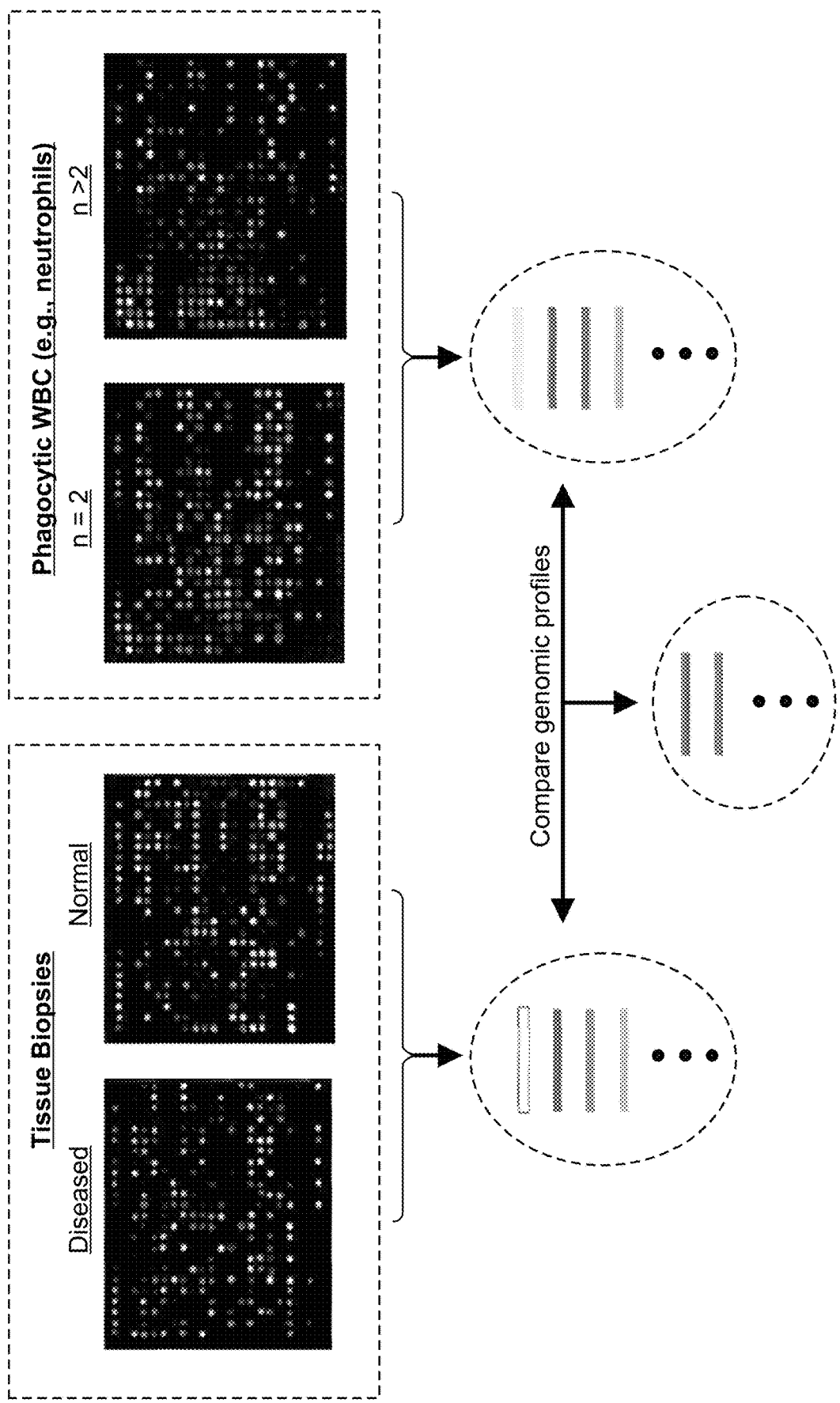
FIG. 6 schematically depicts one embodiment of a method of this invention for identifying autoimmune or immune-related disease or condition-specific markers selectively acquired/expressed by >2n phagocytic cells of a patient.
Figure 7:
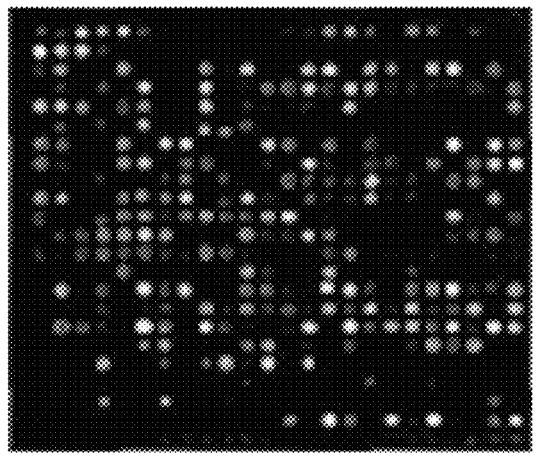
FIG. 7 schematically depicts one embodiment of a method of this invention for diagnosing/detecting an autoimmune or immune-related disease or condition by comparing expression profiles obtained from arrays.
Figure 7:
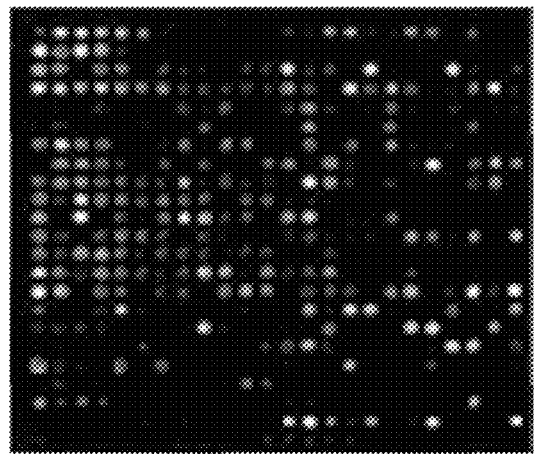
Figure 7:
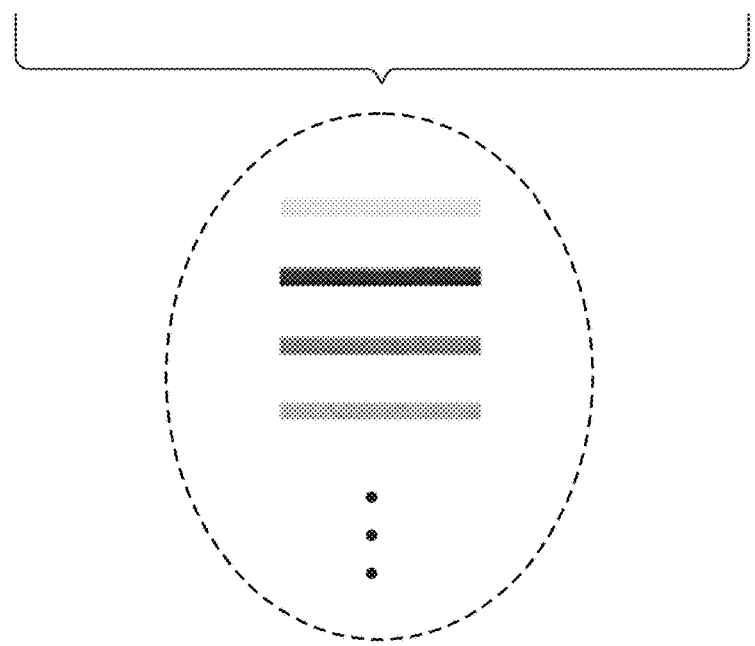
Figure 8:
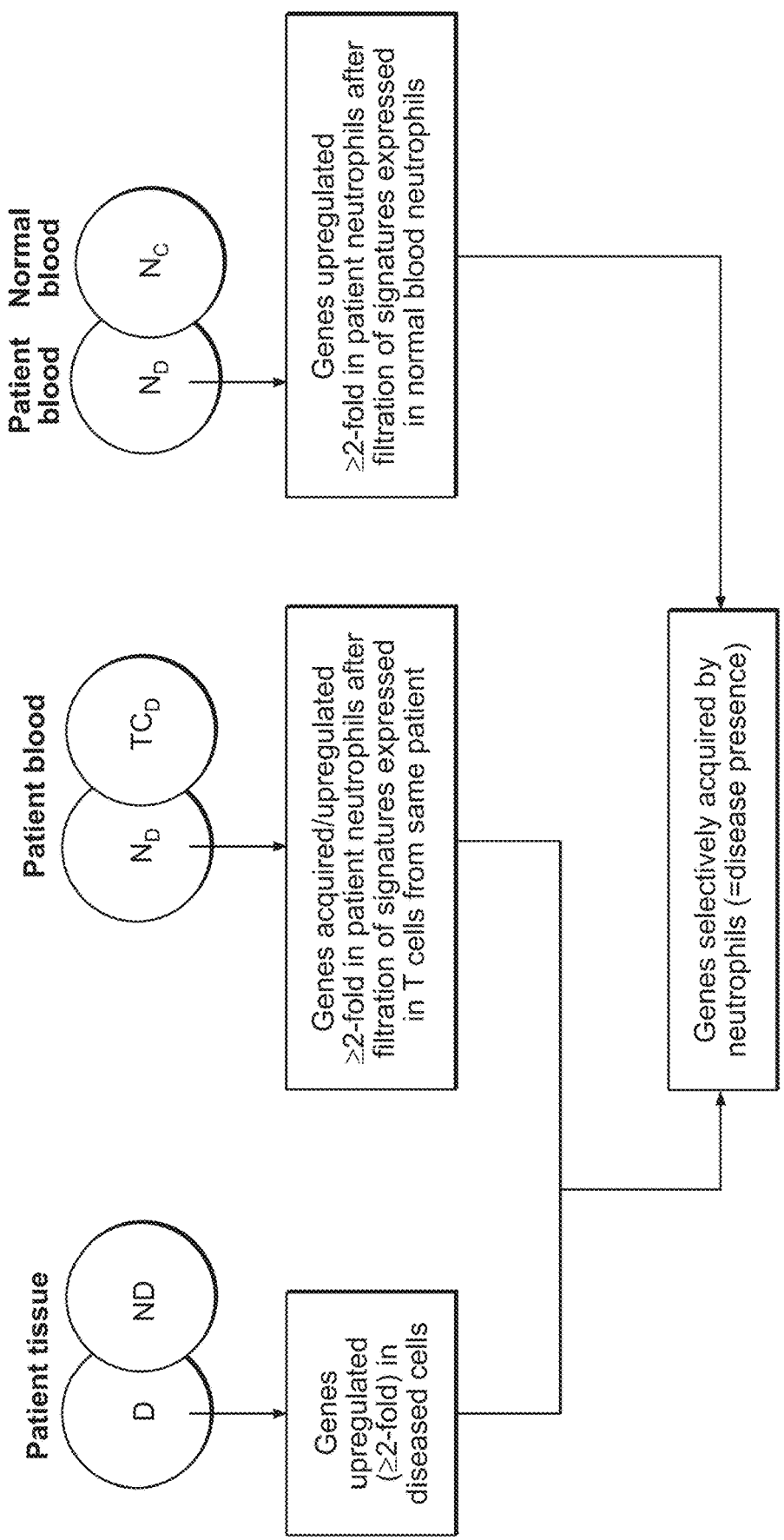
FIG. 8 schematically depicts one embodiment of a method of this invention for identifying one or more markers of an autoimmune or immune-related disease or condition. D represents diseased cells/tissues from a patient having an autoimmune or immune-related disease or condition; and ND represents not-diseased cells/tissues from the patient; $N_D$ represents neutrophils taken from the patient; $TC_D$ represents T cells taken from the patient; $N_C$ represents neutrophils obtained from a control subject not having the disease or condition.

A Representative Method for the Separation of Phagocytic Cells from Non-Phagocytic Cells and the Analysis of Expression Profiles 1. With reference to FIG. 1D, stain WBC with fluorescent antibodies to each cell subpopulation (e.g., neutrophils, macrophages, monocytes, and T cells), and then stain with DNA dye (e.g., propidium iodide).

2. Sort the cells (FACS) into T cells, neutrophils (2n), neutrophils (>2n), macrophages (2n), macrophages (>2n), monocytes (2n), and monocytes (>2n).

3. Isolate RNA from T cells, neutrophils (>2n), macrophages (>2n), and monocytes (>2n). Then prepare cDNA, cRNA and use to differentiate genetic profiles (e.g., disease gene array) of phagocytic and non-phagocytic cells.

4. Isolate DNA from T cells, neutrophils (>2n), macrophages (>2n), and monocytes (>2n). Run DNA arrays and compare the profiles obtained in phagocytic and nonphagocytic cells.

5. Isolate protein from T cells, neutrophils (>2n), macrophages (>2n), and monocytes (>2n). Run Western blots using antibodies to known proteins overexpressed in an individual with an autoimmune or immune-related disease or condition, and compare the profiles obtained in phagocytic and non-phagocytic cells. Alternatively, use mass spectroscopy to identify the proteins.

6. Isolate lipids from T cells, neutrophils (>2n), macrophages (>2n), and monocytes (>2n). Compare quantity and quality of lipids, for example using HPLC.

What is claimed is:

1. An assay for detecting a marker of an autoimmune or immune-related disease or condition in a human subject, wherein the autoimmune or immune-related disease or condition is multiple sclerosis or inflammatory bowel disease, the assay comprising:
   a) obtaining a macrophage having a DNA content of more than 2n (>2n macrophage cell) from the blood of the human subject, wherein the >2n macrophage has been separated from phagocytic cells having a DNA content of 2n (=2n phagocytic cells), and detecting a first gene expression profile of the marker of an autoimmune or immune-related disease or condition; and
   b) obtaining a non-phagocytic cell from the blood of the human subject and detecting a second gene expression profile of the marker of an autoimmune or immune-related disease or condition in the obtained non-phagocytic cell.

2. The assay of claim 1, further comprising lysing the >2n macrophage and the non-phagocytic cell before performing the detecting.

3. The assay of claim 1, further comprising extracting cellular contents from the >2n macrophage and the non-phagocytic cell before performing the detecting.

4. The assay of claim 3, wherein the cellular contents of the >2n macrophage comprises viable diseased cells, dead diseased cells, apoptotic diseased cells, circulating tumor cells, infectious agents, fetal cells, trophoblasts, or fragments thereof.

5. The assay of claim 1, wherein the >2n macrophage and the non-phagocytic cell are obtained from a bodily fluid sample, tissues, or cells of the subject.

* * * * *

UNITED STATES PATENT AND TRADEMARK OFFICE
CERTIFICATE OF CORRECTION

| | |
|---|---|
| PATENT NO. | : 11,111,537 B2 |
| APPLICATION NO. | : 15/014476 |
| DATED | : September 7, 2021 |
| INVENTOR(S) | : Amin I. Kassis |

It is certified that error appears in the above-identified patent and that said Letters Patent is hereby corrected as shown below:

In the Specification

At Column 1, Line 16, please add the following paragraph before the FIELD OF THE INVENTION as follows:
— GOVERNMENT SUPPORT CLAUSE
This invention was made with government support under W81XWH-09-1-0210 awarded by U.S. Army Medical Research and Materiel Command (MRMC). The government has certain rights in this invention. —

Signed and Sealed this
Fifteenth Day of November, 2022

Katherine Kelly Vidal
*Director of the United States Patent and Trademark Office*